United States Patent
Doyle et al.

(10) Patent No.: US 8,105,982 B2
(45) Date of Patent: Jan. 31, 2012

(54) APTAMERS AND METHODS FOR THEIR IN VITRO SELECTION AND USES THEREOF

(75) Inventors: Sharon A. Doyle, Walnut Creek, CA (US); Michael B. Murphy, Severna Park, MD (US)

(73) Assignee: The Regents of the University of California, Oakland, CA (US)

( * ) Notice: Subject to any disclaimer, the term of this patent is extended or adjusted under 35 U.S.C. 154(b) by 689 days.

(21) Appl. No.: 12/027,239

(22) Filed: Feb. 6, 2008

(65) Prior Publication Data

US 2009/0075834 A1 Mar. 19, 2009

Related U.S. Application Data

(62) Division of application No. 10/934,856, filed on Sep. 3, 2004, now Pat. No. 7,329,742.

(60) Provisional application No. 60/500,800, filed on Sep. 4, 2003, provisional application No. 60/584,591, filed on Jun. 30, 2004.

(51) Int. Cl.
*C07H 21/02* (2006.01)
*C40B 20/04* (2006.01)
*C40B 30/04* (2006.01)

(52) U.S. Cl. .................. 506/4; 506/9; 536/23.1

(58) Field of Classification Search ............. 536/23.1; 506/4, 9
See application file for complete search history.

(56) References Cited

U.S. PATENT DOCUMENTS

| | | | |
|---|---|---|---|
| 5,756,291 A | 5/1998 | Griffin et al. | |
| 5,843,653 A | 12/1998 | Gold et al. | |
| 6,180,348 B1 | 1/2001 | Li et al. | |
| 6,350,580 B1 | 2/2002 | Sorge et al. | |
| 6,423,493 B1 | 7/2002 | Gorenstein et al. | |
| 6,475,736 B1 | 11/2002 | Stanton et al. | |
| 6,515,120 B1 * | 2/2003 | Kwagh et al. | 536/25.4 |
| 6,747,135 B1 | 6/2004 | Nolan et al. | |
| 6,914,137 B2 * | 7/2005 | Baker | 536/25.4 |
| 7,125,660 B2 * | 10/2006 | Stanton et al. | 435/4 |
| 2001/0018513 A1 * | 8/2001 | Baker | 536/25.41 |
| 2003/0054360 A1 * | 3/2003 | Gold et al. | 435/6 |

OTHER PUBLICATIONS

Cox JC, Rajendran M, Riedel T, Davidson EA, Sooter LJ, Bayer TS, Schmitz-Brown M, Ellington AD. (2002) Automated acquisition of aptamer sequences. *Comb Chem High Throughput Screen.* Jun;5(4):289-99.
Cox JC, Hayhurst A, Hesselberth J, Bayer TS, Georgiou G, Ellington AD. Automated selection of aptamers against protein targets translated in vitro: from gene to aptamer, Nucleic Acids Res. Oct. 15, 2002;30(20):e108.
Ellington AD, Szostak JW. (1990) In vitro selection of RNA molecules that bind specific ligands. *Nature.* Aug. 30;346(6287):818-22.
Ellington AD, Szostak JW. (1992) Selection in vitro of single-stranded DNA molecules that fold into specific ligand-binding structures. *Nature.* Feb. 27;355(6363):850-2.
Drolet DW, Jenison RD, Smith DE, Pratt D, Hicke BJ. (1999) A high throughput platform for systematic evolution of ligands by exponential enrichment (SELEX). *Comb Chem High Throughput Screen.* Oct;2(5):271-8.
Romig TS, Bell C, Drolet DW. Aptamer affinity chromatography: combinatorial chemistry applied to protein purification, J Chromatogr B Biomed Sci Appl. Aug. 20, 1999;731(2):275-84.
Tuerk C, Gold L. (1990) Systematic evolution of ligands by exponential enrichment: RNA ligands to bacteriophage T4 DNA polymerase. *Science.* Aug. 3;249(4968):505-10.
Walter G, Bussow K, Lueking A, Glokler J. (2002) High-throughput protein arrays: prospects for molecular diagnostics. *Trends Mol Med.* Jun;8(6):250-3.
Ylera F, Lurz R, Erdmann VA, Furste JP. (2002) Selection of RNA aptamers to the Alzheimer's disease amyloid peptide. *Biochem Biophys Res Commun.* Feb. 8;290(5):1583-).

* cited by examiner

*Primary Examiner* — Amber D. Steele
(74) *Attorney, Agent, or Firm* — Michelle Chew Wong; Lawrence Berkeley Nat'l Laboratory

(57) ABSTRACT

The present method is an improved in vitro selection protocol that relies on magnetic separations for DNA aptamer production that is relatively easy and scalable without the need for expensive robotics. The ability of aptamers selected by this method to recognize and bind their target protein with high affinity and specificity, and detail their uses in a number of assays is also described. Specific TTF1 and His6 aptamers were selected using the method described, and shown to be useful for enzyme-linked assays, Western blots, and affinity purification.

8 Claims, 15 Drawing Sheets

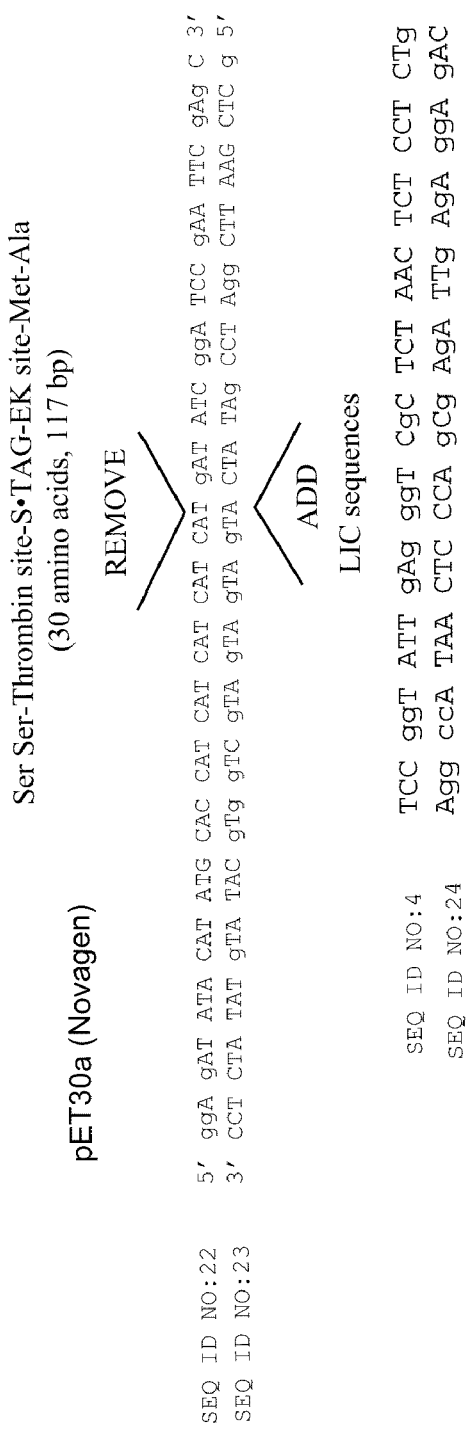

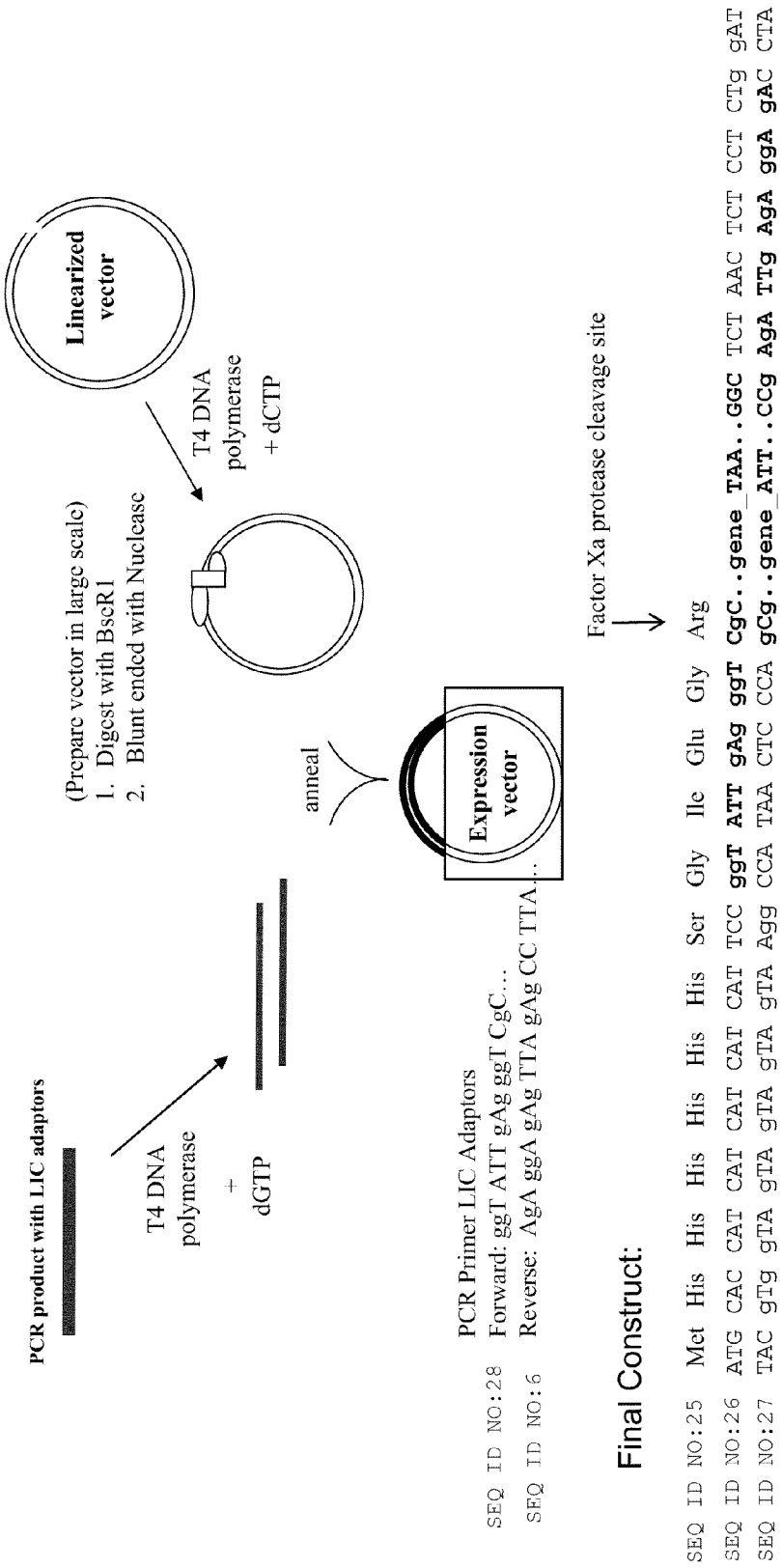

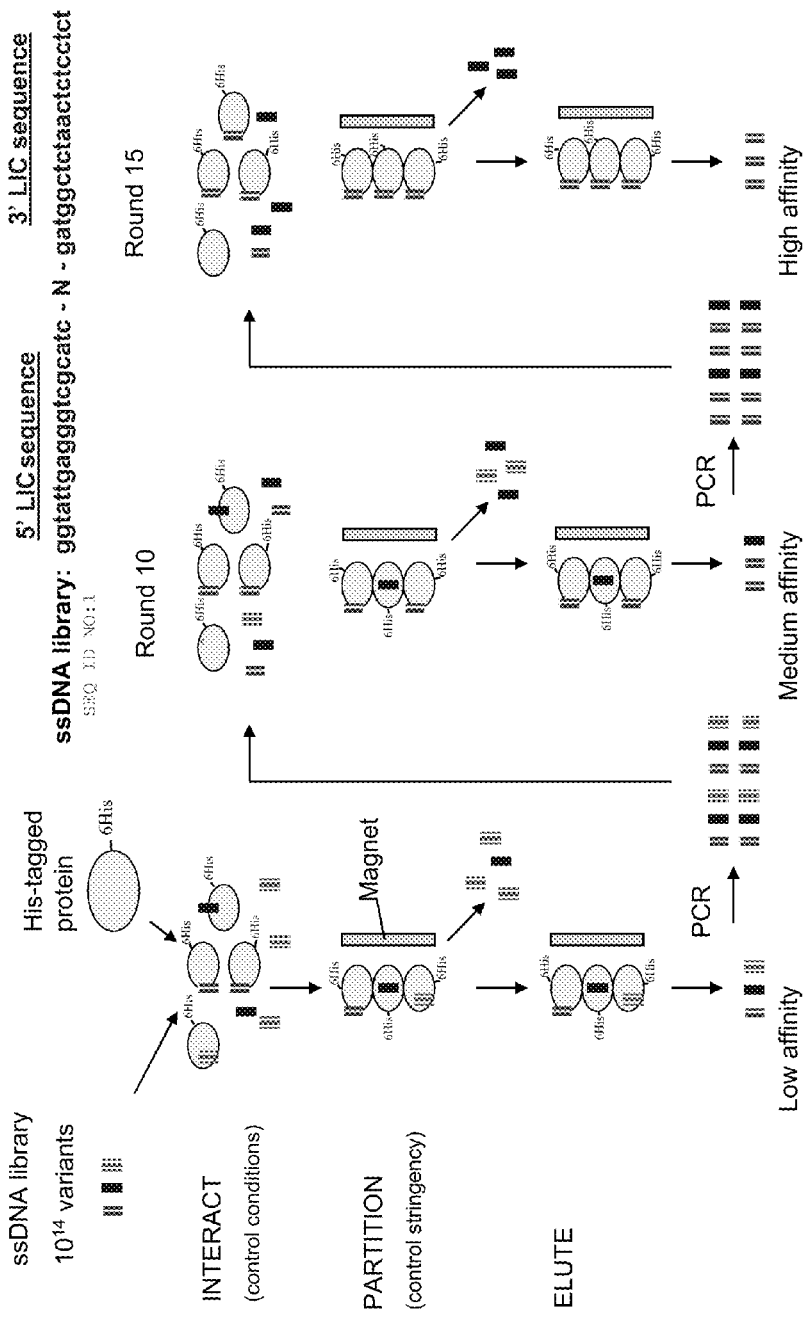

Figure 4

Enrichment of Aptamers to TTF1 from 15 Rounds of Selection. The 40 base variable region of each aptamer sequence is shown (5'-3'). The number of times that each sequence was obtained from a total of 30 isolates is displayed on the right. A consensus found in two of the aptamers is underlined.

| | Aptamer | Variable Sequence | Enrichment |
|---|---|---|---|
| SEQ ID NO:9 | A | tcaaaaggggtgattgcttgcacaatgacagggtaggaca | 9 |
| SEQ ID NO:10 | B | gatacacgggcggaggagtggggggggtaggtgggtat | 7 |
| SEQ ID NO:11 | C | tggctagtgggtaaggggcggagggtgacagggcgatcc | 6 |
| SEQ ID NO:12 | D | ttatggggatgaaagtggtgtgtgtgtgtcgggttcgccacttccac | 3 |
| SEQ ID NO:13 | E | ttggggtgggaggcgcgggtaacaaagatagcgcaacagg | 2 |

Figure 9

|       |   |                                                              |                |
|-------|---|--------------------------------------------------------------|----------------|
| 6H1   | 1 | GGCAAAAAGGATTGCCCAGGTCTGTCTAGCCGGATTC----                    | SEQ ID NO:15   |
| 6H5   | 1 | GGCTTC--AGGTTGGTTGGTCCTGGCTCCTGTACG--                        | SEQ ID NO:14   |
| 6H7   | 1 | -GCTAT--GGGT--GGTTGGATTGGCCCGGAGCTGGC                        | SEQ ID NO:16   |
| Consensus | 1 | GGCTA GGGTTGGTCTGGTTTGGC CCGG TC G                       | SEQ ID NO:21   | positives: 79.5%   identity: 31.8%

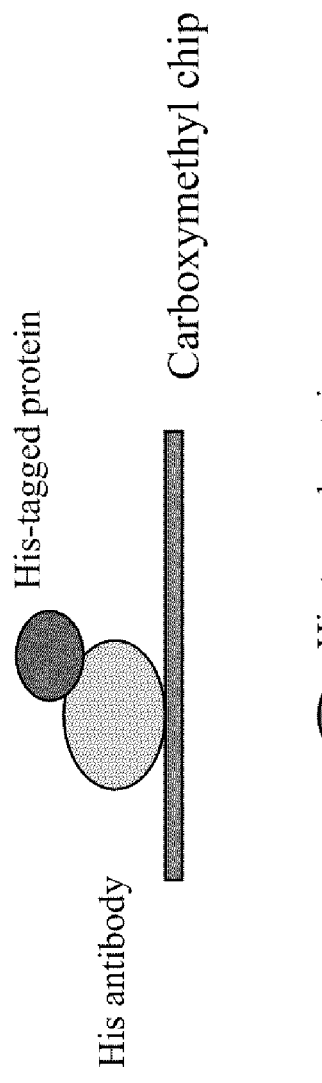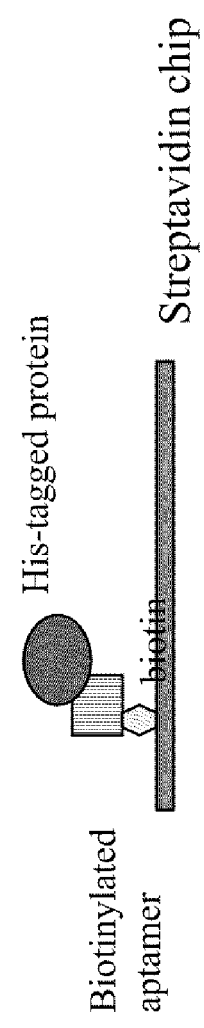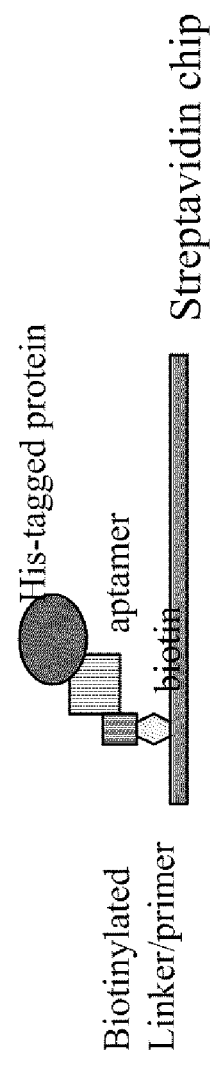
Figure 10

APTAMERS AND METHODS FOR THEIR IN VITRO SELECTION AND USES THEREOF

CROSS REFERENCE TO RELATED APPLICATION

This application relates to and claims benefit of Provisional Patent Application Ser. No. 60/500,800, filed Sep. 4, 2003, and Provisional Patent Application Ser. No. 60/584,591, filed Jun. 30, 2004, and is a divisional application to U.S. patent application Ser. No. 10/934,856, filed on Sep. 3, 2004, to be issued as U.S. Pat. No. 7,329,742, all of which are hereby incorporated by reference in their entirety.

REFERENCE TO SEQUENCE LISTING, TABLE, OR COMPUTER PROGRAM APPENDIX

Applicants assert that the attached paper copy of the Sequence Listing for the utility application, "Aptamers and methods for their in vitro selection and uses thereof," claiming priority to U.S. Provisional Patent Application No. 60/500,800 filed Sep. 4, 2003, and Provisional Patent Application Ser. No. 60/584,591, filed Jun. 30, 2004, is identical to the Sequence Listing in computer readable form also attached as a .txt file, "IB1929_SEQLISTING8.txt", created on Jul. 6, 2007, as required by 37 CFR 1.821(c), both of which are hereby incorporated by reference in their entirety.

STATEMENT OF GOVERNMENT SUPPORT

This invention was made during work supported by the U.S. Department of Energy at Lawrence Livermore National Laboratory under contract No. W-7405-ENG-48, Lawrence Berkeley National Laboratory under contract No. DE-AC03-76SF00098, and Los Alamos National Laboratory under contract No. W-7405-ENG-36. The government has certain rights in this invention.

BACKGROUND OF THE INVENTION

1. Field of the Invention

This invention relates to aptamers and methods for the selection and generation of aptamers for use in such fields of application as proteomics, protein detection and purification, drug design and development, and protein purification and capture reagents.

2. Prior Relevant Art

The future success of proteomics depends on its ability to follow in the footsteps of genomics, where the development of new technologies generated an abundance of sequence data enabling researchers to probe problems that relate to the entire nucleic acid component of the cell. For the promise of proteomics to be realized, new tools are needed that will enable large-scale investigations of protein structure, function, and interactions. Significant progress has been made in proteomic technology development in many areas, including high-throughput gene cloning, protein production, mass spectrometry, 2-D PAGE, and microfluidics to allow large-scale proteomics to proceed.

One important set of tools that has been improved with moderate success are affinity reagents that function as antibodies to serve as protein probes. Affinity molecules that specifically bind proteins of interest can detect bound proteins in a protein microarray, or capture protein complexes for functional identification. Often these molecules can alter biological activity due to their binding and inhibit critical interactions by sterically blocking access to active sites and interaction surfaces, and thus present an opportunity to serve as functional probes as well as therapeutics. Traditionally, antibodies have satisfied the demand for such ligands, however as recombinant protein production gains throughput and pharmaceutical target repertoires expand, the ability to efficiently generate antibodies quickly falls short.

Several alternatives to antibodies have been investigated, such as single chain antibodies (scFv), peptides displayed on protein domain scaffolded surfaces, peptides, and peptoids (synthetic peptides). Each of these alternatives has drawbacks that limit their uses, such as problems of stability in varying conditions (ionic strength, temperature, and pH) and of low affinity, making some antibody alternatives ineffective for detecting proteins under many conditions.

The use of aptamers as protein affinity reagents offers advantages over the use of antibodies. Nucleic acids are easily synthesized or amplified by PCR; therefore a vast supply of consistent quality is available. Also, nucleic acids can easily be modified to incorporate tags, such as biotin or fluorescent molecules, for detection and/or immobilization. Additionally, aptamers are smaller (<25 kDa) and more stable than antibodies. Moreover, unlike the requirement of milligram quantities of protein or peptide for antibody production, only microgram quantities of protein or peptide are required for aptamer selection. These properties, coupled with the present technology available for DNA microarrays, make aptamers very suitable for use in protein microarrays as a ligand, or for detecting proteins bound to a chip surface (See Walter G, Bussow K, Lueking A, Glokler J. (2002) High-throughput protein arrays: prospects for molecular diagnostics. *Trends Mol. Med.* June; 8(6):250-3).

The idea of using single stranded nucleic acids (aptamers) as affinity molecules for proteins has shown modest progress. See Tuerk C, Gold L. (1990) Systematic evolution of ligands by exponential enrichment: RNA ligands to bacteriophage T4 DNA polymerase. *Science.* August 3; 249(4968):505-10; Ellington A D, Szostak J W. (1990) In vitro selection of RNA molecules that bind specific ligands. *Nature.* August 30; 346 (6287):818-22; and Ellington A D, Szostak J W. (1992) Selection in vitro of single-stranded DNA molecules that fold into specific ligand-binding structures. *Nature.* February 27; 355 (6363):850-2. The concept is based on the ability of short oligomer (20-80 mer) sequences to fold, in the presence of a target, into unique 3-dimensional structures that bind the target with high affinity and specificity. Aptamers are generated by a process that combines combinatorial chemistry with in vitro evolution, commonly known as SELEX (Systematic Evolution of Ligands by Exponential Enrichment). Following the incubation of a protein with a library of DNA or RNA sequences (typically $10^{14}$ molecules in complexity) protein-DNA complexes are isolated, the DNA is amplified, and the process is repeated until the sample is enriched with sequences that display high affinity for the protein of interest. Since the selection pressure is high affinity for the target, aptamers with low nanomolar affinities may be obtained. Aptamers offer advantages over protein-based affinity reagents because nucleic acids possess increased stability, ease of regeneration (PCR or oligonucleotide synthesis), and simple modification for detection and immobilization.

Although SELEX appears to be technically very simple, small alterations to a protocol can have a large impact on the success of generating aptamers. Perhaps this explains why thirteen years since its first citation in the literature, only approximately forty protein-detecting aptamer sequences have been published, and very few have been well characterized. Although high-throughput methods for aptamer production have been published, most require expensive robotics and have not produced aptamers against large numbers of diverse targets (Cox J C, Rajendran M, Riedel T, Davidson E A, Sooter L J, Bayer T S, Schmitz-Brown M, Ellington A D. (2002) Automated acquisition of aptamer sequences. *Comb Chem High Throughput Screen*. June; 5(4):289-99).

Many variations in aptamer production protocols have been described in which the method of protein target partitioning seems to vary the most. Unbound DNA molecules have been removed from target proteins via: 1) filtration on a membrane (Ellington A D, Szostak J W. (1992) Selection in vitro of single-stranded DNA molecules that fold into specific ligand-binding structures. *Nature*. February 27; 355(6363): 850-2); 2) column chromatography, in which the targets are bound to a matrix, such as sepharose, using a covalent linkage or an affinity tag (Ylera F, Lurz R, Erdmann V A, Furste J P. (2002) Selection of RNA aptamers to the Alzheimer's disease amyloid peptide. *Biochem Biophys Res Commun*. February 8; 290(5):1583-); and 3) binding of the protein to the wells of a microtiter plate (Drolet D W, Jenison R D, Smith D E, Pratt D, Hicke B J. (1999) A high throughput platform for systematic evolution of ligands by exponential enrichment (SELEX). *Comb Chem High Throughput Screen*. October; 2(5):271-8).

Gorenstein, et al, in U.S. Pat. No. 6,423,493, describe a random combinatorial selection method for the construction of oligonucleotide aptamers in which nuclease resistance is conferred by the inclusion of modified nucleotides. The modified nucleotides are incorporated during PCR amplification to form achiral modified oligonucleotides. Thio-substituted aptamers are provided that bind tightly to the nuclear factor for human IL6 (NF-IL6).

Kwagh, et al., in U.S. Pat. No. 6,515,120, describe a method for sequencing and structurally characterizing a polymeric biomolecule using aptamers and also describes aptamers that recognize and bind to AMP, dAMP, GMP, dGMP, CMP and dCMP.

In U.S. Pat. No. 6,180,348, Li describes a method that makes use of magnetic separation to identify an aptamer which specifically binds to a target molecule of interest. A method for identifying oligomer sequences, optionally comprising modified bases, which specifically bind target molecules such as serum proteins, kinins, eicosanoids and extracellular proteins is described by Griffin, et al in U.S. Pat. No. 5,756,291. The method is used to generate aptamers that bind to serum Factor X, PDGF, FGF, ICAM, VCAM, E-selectin, thrombin, bradykinin, PGF2 and cell surface molecules.

SUMMARY OF THE INVENTION

The invention provides for a method for obtaining an aptamer having high affinity to a target molecule, comprising: (a) preparing a target molecule with a polyhistidine affinity tag for magnetic beads; (b) binding the target molecule to magnetic beads and contacting the target molecule with a library of aptamer sequences to allow binding of aptamer sequences to the target molecule thus forming bead-target-aptamer sequence complexes, wherein the aptamer sequences are comprised of degenerate sequences; (c) separating bead-target-aptamer sequence complexes from non-binding aptamer sequences by retaining the target molecule on its bead and removing unbound aptamer sequences; then (d) separating target-bound aptamer sequences from said magnetic beads to form a pool of binding aptamer sequences; (e) amplifying the binding aptamer sequences; and (f) iteratively repeating steps (b) through (d) a sufficient number of times to result in identification of at least one aptamer sequence having high affinity for the target molecule.

The method further comprising: subcloning the high affinity aptamer sequence into a plasmid and transforming *E. coli*; isolating said plasmid containing said aptamer sequence from transformed *E. coli*; and amplifying and sequencing said cloned aptamer sequence.

In one embodiment, the magnetic beads are Ni-coated. In another embodiment, the targets are hexahistidine-tagged proteins.

In one aspect, an aptamer of the present invention is a single stranded DNA sequence, although RNA or other amplifiable nucleic acid based polymers can be used. In a preferred embodiment, the aptamer sequence is degenerate random sequence about 20-50 bases long. In another embodiment the aptamer further comprises the degenerate sequence flanked by fixed sequences. In a preferred embodiment, the flanking fixed sequences permit ligation-independent cloning. In another embodiment, the flanking fixed sequences are primer sequences that can be biotinylated In another aspect, a library of $10^8$ to $10^{15}$ random aptamers is first generated and incubated with the target molecule. The unbound aptamers are washed away. The aptamers bound to the targets are eluted and amplified by PCR to form a new pool for another round of binding to the targets.

In another embodiment, the method can further comprise: subcloning the high affinity aptamer sequence into a plasmid and transforming *E. coli* with the affinity aptamer sequence; isolating the plasmid clone containing the aptamer sequence from the transformed *E. coli*; and amplifying and sequencing the cloned aptamer sequence. In a preferred embodiment, the plasmid is selected from the group consisting of pUC18LIC and pET30XaLIC, and amplification is by rolling circle amplification.

In another embodiment, the magnetic beads are streptavidin coated and the targets are His6 peptides or proteins tagged with biotin to generate aptamers against a His6 peptide. In this embodiment, the His6 peptide tagged with biotin facilitates the attachment of the His6 peptide to streptavidin magnetic beads.

The invention also describes novel nucleic acid molecules or aptamers generated by the methods of the invention. The invention further provides for aptamers generated by the method described herein, wherein the aptamers have high binding affinity to thyroid transcription factor 1 (TTF1) protein. The TTF1 aptamer comprising a sequence having at least 90% homology to a sequence selected from the group consisting of SEQ ID NO: 9, SEQ ID NO: 10, SEQ ID NO: 11, SEQ ID NO: 12, and SEQ ID NO: 13. The aptamer sequence can further comprise flanking fixed sequences. In one embodiment, the flanking fixed sequences are primers such as SEQ ID NO: 17 and SEQ ID NO: 18, wherein one of the primers is biotinylated.

In another embodiment, aptamers were generated to a polyhistidine (His6). These His6 aptamers, the sequences of which are herein described, are useful for the capture and detection of proteins that contain at least 5, normally 6 or more histidine residues (His6) fused to target peptides, proteins and biomolecules. The His6 aptamers comprising a sequence having at least 90% homology to a sequence selected from the group consisting of SEQ ID NO: 14, SEQ ID NO: 15, and SEQ ID NO: 16. The aptamer sequence can further comprise flanking fixed sequences. In one embodiment, the flanking fixed sequences are primers such as SEQ ID NO: 17 and SEQ ID NO: 18, wherein one of the primers is biotinylated.

The invention further contemplates that these aptamer sequences may be varied in the degenerate sequence region, by up to 20 percent, more preferably by 10 percent, most preferably by 5 percent, while retaining the functional properties as described herein.

The invention also provides a method for obtaining a His6 aptamer having high affinity to a target molecule, comprising: (a) preparing a target polyhistidine molecule with an affinity tag for magnetic beads; (b) binding the target molecule to magnetic beads and contacting the target molecule with a library of aptamers of different sequences to allow binding of aptamer sequences to the target molecule thus forming bead-target-aptamer sequence complexes; (c) separating bead-target-aptamer sequence complexes from non-binding aptamers by retaining the target molecule on its bead and removing unbound aptamers; then (d) separating target-bound aptamers from said magnetic beads to form a pool of binding aptamers; (e) amplifying the binding aptamers; and (f) iteratively repeating steps (b) through (d) a sufficient number of times to result in identification of at least one aptamer sequence having high affinity for the target molecule. In one embodiment, the magnetic beads are streptavidin-coated and the target polyhistidine molecule is biotinylated. The invention further provides for an aptamer isolated by the method described, wherein the aptamer effectively binds to a polyhistidine residue tag. In another aspect, the sequence of the aptamer is at least 80% homologous to SEQ ID NO: 14, 15 or 16.

One embodiment of the present invention involves preparing a library of protein-binding aptamers for use with complex mixtures of proteins. Because of the stability of the present aptamers, they may be immobilized on chips or microarrays. They may be used to isolate and purify proteins as well.

The invention further provides for a method of protein purification comprising the steps of: (a) providing an affinity column, wherein the affinity tag is an aptamer isolated by the methods described; and (b) applying a crude extract or culture from which a target protein is to be isolated. In one embodiment, the affinity tag is a His6 aptamer and the target protein has a polyhistidine tag. In a preferred embodiment, the His6 aptamer is at least 80% homologous to SEQ ID NO: 14, 15 or 16.

It is further an object of the disclosed invention to provide aptamers that bind sequential histidine amino acid residues or to sequential histidine amino acid residues fused to any other amino acid residues or protein. The invention also contemplates the use of these His6 aptamers in biological applications, including the use with solid supports for affinity resins, magnetic or polymer beads, as a diagnostic detection reagent, to capture or immobilize reagents for diagnostic, detection or quantitative studies.

The invention provides for an apparatus comprising: (a) a solid support; and (b) an His6 aptamer or an array of His6 aptamers attached to the solid support. In one aspect, the solid support is comprised of glass, metal silicon, ceramic or polymer. The apparatus further comprises a peptide or protein bound to the aptamer. The peptide or protein binds to the His6 aptamer by means of a polyhistidine tag. In a preferred embodiment, the His6 aptamer is at least 80% homologous to SEQ ID NO: 14, 15 or 16.

In another aspect, the solid support is coated with at least one material selected from the group consisting of gold, avidin, streptavidin, carboxymethyl groups, dextran or collagen. In one embodiment, the solid support is coated with streptavidin and the aptamer is biotinylated, whereby the aptamer attaches to the solid support through the binding of biotin and the streptavidin-coating.

In one embodiment, the His6 aptamer is attached to the solid support by means of an oligonucleotide. In this embodiment, the oligonucleotide is biotinylated and attaches to the solid support through the binding of biotin and the streptavidin-coating. In one aspect, the aptamer would further comprise flanking primer sequences, whereby at least 3 bases of the flanking primer sequences of the aptamer has base complementarity to the oligonucleotide. In another aspect, the invention further comprising a peptide or protein bound to the aptamer by means of a polyhistidine tag.

It is also an object of the invention to provide a method of capturing a molecule of interest, comprising the steps of: (a) providing a solid support having an aptamer or array of aptamers attached to the support, wherein the aptamer comprises a sequence having at least 90% homology to SEQ ID NO: 14, SEQ ID NO: 15 or SEQ ID NO: 16; (b) applying a sample containing a molecule of interest having a polyhistidine tag to the support; (c) capturing the molecule of interest.

In one aspect, the solid support comprises glass, metal ceramic or polymeric materials. The solid support can be selected from the group consisting of steel, gold, silver, aluminum, copper, silicon, glass, polyethylene, polypropylene, polyamide, and polyvinylidenefluoride, and combinations thereof. In another aspect, the solid support is coated with a material to facilitate the attachment, binding, hybridization, immobilization or interaction of the aptamer on the surface. In a preferred embodiment, the coating comprises gold, carboxymethylation, dextran, collagen, avidin or streptavidin.

DESCRIPTION OF THE FIGURES

FIG. 1 shows the method of constructing an N-terminal 6×His tag vector for Ligation Independent Cloning (LIC).

FIG. 2 shows the High-throughput Cloning Method with LIC.

FIG. 3 is a cartoon which shows the In Vitro Selection Protocol for the production of ssDNA ligands or aptamers that bind targets with high affinity and specificity.

FIG. 4 shows the selected aptamers to TTF1 enriched from 15 rounds of selection. The 40 base variable region of each aptamer sequence is shown (5'-3'). The number of times that each sequence was obtained from a total of 30 isolates is displayed on the right. A consensus sequence found in two of the aptamers is underlined.

FIG. 9 is a copy of the display output showing the aptamer sequence alignment for the His6 aptamers 6H1, 6H5 and 6H7.

FIG. 10 is a schematic showing various capture methods for SPR applications including (A) traditional methods using an antibody that binds to a His6 tag, (B) use of a biotinylated aptamer on a streptavidin chip that binds to a His6 tag, and (C) use of a biotinylated linker/primer on a streptavidin (SA) chip that binds to a fixed portion of the aptamer by base complementarity.

DETAILED DESCRIPTION OF THE PREFERRED EMBODIMENT

I. Introduction

Figure 5:
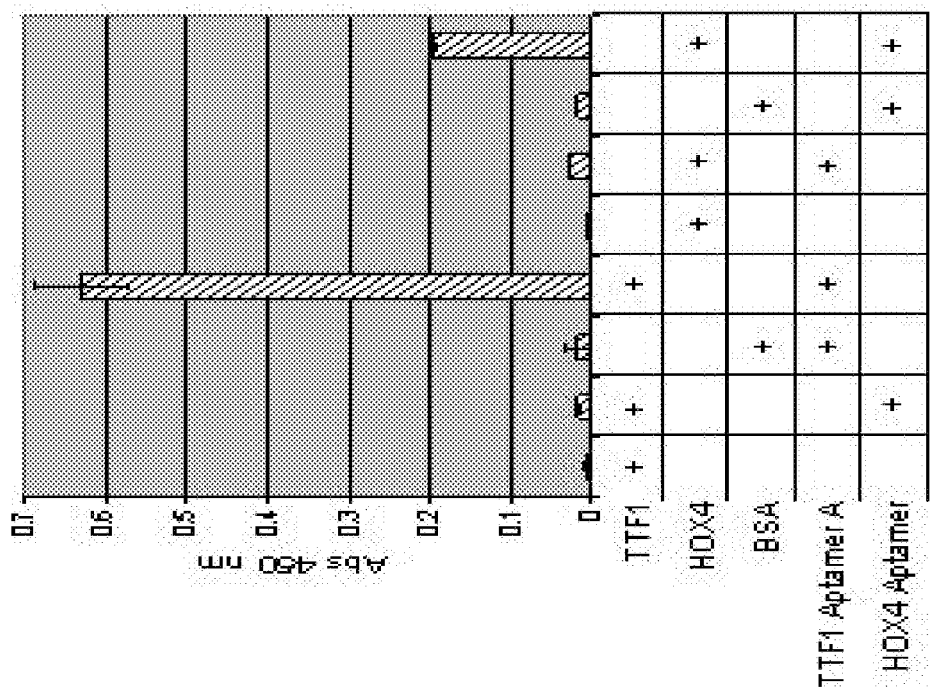
FIG. 5 is a graph showing the determination of specificity of aptamers using an enzyme-linked assay. Combinations of TTF1, HOX4, and BSA protein and either a TTF1 aptamer "A" or HOX4 aptamer (indicated by plus signs below the graph) were evaluated for their binding activity and cross-reactivity. The data are from triplicate samples.

The present invention provides for an in vitro ssDNA selection method that utilizes tagged target molecules bound to magnetic beads to screen for high affinity binding aptamers from a library of degenerate sequences. The invention also describes novel nucleic acid molecules or aptamers generated by the methods of the invention. The invention also contemplates the use of these His6 aptamers in biological applications, including the use with solid supports for affinity resins, magnetic or polymer beads, as a diagnostic detection reagent, to capture or immobilize reagents for diagnostic, detection or quantitative studies As used herein, the terms "aptamer(s)" or "aptamer sequence(s)" are meant to refer to single stranded nucleic acids (RNA or DNA) whose distinct nucleotide sequence determines the folding of the molecule into a unique three dimensional structure. Aptamers comprising 15 to 120 nucleotides can be selected in vitro from a randomized pool of oligonucleotides ($10^{14}$-$10^{15}$ molecules). The "aptamers or aptamer sequences" comprise a degenerate sequence, and can further comprise fixed sequences flanking the degenerate sequence. The term "aptamer" as used herein further contemplates the use of both native and modified DNA and RNA bases, e.g. beta-D-Glucosyl-Hydroxymethyluracil.

As used herein, a polynucleotide or fragment thereof is "substantially homologous" (or "substantially similar") to another if, when optimally aligned (with appropriate nucleotide insertions or deletions) with the other polynucleotide (or its complementary strand), using BLASTN (Altschul, S. F., Gish, W., Miller, W., Myers, E. W. & Lipman, D. J. (1990) "Basic local alignment search tool." J. Mol. Biol. 215:403-410) there is nucleotide sequence identity in at least about 80%, preferably at least about 90%, and more preferably at least about 95-98% of the nucleotide bases. To determine homology between two different polynucleotides, the percent homology is to be determined using the BLASTN program "BLAST 2 sequences". This program is available for public use from the National Center for Biotechnology Information (NCBI) over the Internet (Tatiana A. Tatusova, Thomas L. Madden (1999), "Blast 2 sequences—a new tool for comparing protein and nucleotide sequences", FEMS Microbiol Lett. 174:247-250). The parameters to be used are whatever combination of the following yields the highest calculated percent homology (as calculated below) with the default parameters shown in parentheses:
Program—blastn
Reward for a match—0 or 1 (1)
Penalty for a mismatch—0, −1, −2 or −3 (−2)
Open gap penalty—0, 1, 2, 3, 4 or 5 (5)
Extension gap penalty—0 or 1 (1)
Gap x_dropoff—0 or 50 (50)
Expect—10
Word size—11
Filter—low complexity.

II. In Vitro Selection of Aptamer Sequences

The present aptamer selection method generally comprises the following steps: (1) interacting a target molecule (e.g. recombinant protein, peptide, carbohydrate, lipid, glycolipid, etc.) comprising a tag for binding to magnetic beads with a library of aptamer sequences to allow specific interaction and binding of aptamer sequences to the target thus forming bead-target-aptamer sequence complexes; (2) separating bead-target-aptamer sequence complexes from non-binding aptamer sequences using the magnetic beads leaving only the bead-target-aptamer sequence complexes; (3) releasing target-aptamer sequence from said magnetic beads; (4) amplifying aptamer sequences that bound to the target; and (5) repeating steps (1) through (4) a sufficient number of times to result in an aptamer sequence having high affinity for the target.

The method can further comprise the following steps: (1) subcloning the high affinity aptamer sequence into a plasmid and transforming E. coli; (2) isolating said plasmid containing said aptamer sequence from transformed *E. coli*; (3) amplifying and sequencing said cloned aptamer sequence.

In a specific preferred embodiment, the method was optimized to use Ni-coated magnetic beads to provide a universal support for hexahistidine-tagged protein targets as well as to facilitate the rapid partitioning of protein-aptamer complexes from unselected sequence pools. During the course of optimizing the method an enrichment of sequences that were not unique to a particular protein was observed, and therefore counter-selection steps against Ni-coated magnetic beads to prevent enrichment of aptamers that recognize the beads only were incorporated. The number of PCR cycles was also optimized to avoid overamplification and mis-annealed products. The stringency of the selection can be controlled by adjusting the target protein concentrations, the incubation times, the concentrations of solutions and the washes.

The preferred method was also used to facilitate DNA aptamer production and characterization of aptamers that recognize thyroid transcription factor 1 (TTF1), a member of the NK homeodomain transcription factors, and aptamers to the polyhistidine tag to recognize His6 tagged proteins and peptides.

A. Target Molecules

In the present DNA aptamer selection method, a target molecule can be any molecule capable of forming a complex with an oligonucleotide, including, but not limited to, peptides, proteins, enzymes, receptors, antibodies, hormones, glycoproteins, polymers, polysaccharides, nucleic acids, carbohydrates, lipids, sphingolipids, small organic compounds such as drugs, dyes, metabolites, cofactors, transition state analogs and toxins.

Specific target molecules of interest include molecules of biological and physiological relevance in both prokaryotic and eukaryotic organisms, particularly mammals. Examples of such biologically significant molecules in mammals include, but are not limited to, erythropoietin, tissue plasminogen activator, granular colony stimulating factor (G-CSF), growth hormone (GH), endostatin (O'Reilly et al., (1997) Cell 88:277-285), interferons, interleukins, chemokines (Shi et al., (1997) FASEB J. 11: 1330; Bubrovsky et al., (1996) PNAS, USA 92:700-709), enzymes such as SOD (Yoshikai et al., (1995) Cancer Res. 55(8) 1617-1620) and amylase, antibodies (particularly the constant "Fc" regions thereof), OKT3 (Ho et al., (1998) Science 280:1866-1867), serum proteins (e.g., Factor VIII (Papadopulos-Eleopulos et al., (1990) Genetica 95:35-50), Factor VIX, plasminogen, antithrombin III (Jones et al., (1992) Br. J. Cancer 66:744-747), albumin, protein C (Griffin et al., (1993) Blood 82:1989-93), etc.), and vaccines (e.q., HbsAg (Davis et al., (1994) Vaccine 12:1503-1509), etc.). The physiological significance of most of these, and many other molecules, may similarly be found in Goodman and Gilman's The Pharmacological Basis of Therapeutics, 8.sup.th ed., (1990) Pergamon Press, Elmsford, N.Y. Those of skill in the art will appreciate that a virtually unlimited number of other target molecules may also be used with the claimed methods.

For several of the Examples, thyroid transcription factor 1 (TTF1) was chosen as the target molecule. It was recently learned that TTF1 is a highly specific marker for primary lung adenocarcinomas, and antibodies against TTF1 have been recommended to be included in a panel of antibodies for the differential diagnosis between primary and metastatic adenocarcinomas of the lung (Reis-Filho J S, Carrilho C, Valenti C, Leitao D, Ribeiro C A, Ribeiro S G, Schmitt F C. (2000) Is TTF1 a good immunohistochemical marker to distinguish primary from metastatic lung adenocarcinomas? *Pathol Res Pract* 196(12):835-40). Therefore, the TTF1 aptamers described herein may be a valuable diagnostic tool for diseases such as primary lung adenocarcinoma.

B. Magnetic Beads for Immobilization of Tagged Targets

Upon choosing the desired target molecule, the target molecule should be tagged to allow immobilization to the magnetic beads. The use of a tag for immobilization promotes the proper orientation of proteins uniformly on a bead surface, and reduces the chances of selection toward contaminants. Magnetic beads are an optimal solid support for parallel processing of both proteins and nucleic acids. Microliter amounts of magnetic beads with bound target molecules can be rapidly partitioned from unselected material, stringently washed, and subsequently eluted.

Magnetic beads that are coated with molecules having a specific binding partner that can be used as a tag, include, but are not limited to, antibodies, enzymes, antigens, sugars, saccharides, small molecules, amino and polar groups.

In one embodiment, the target molecules are tagged by a commonly used tag such as, a polyhistidine, such as hexahistidine (His6), which binds to nickel (Ni), or streptavidin which binds to biotin. While various tags for binding to affinity supports are known, a preferred tag in this case is polyhistidine for binding to a magnetic bead. Hexahistidine tags are widely used in recombinant protein production. For example, the inventors have described an efficient protein production pipeline for high-throughput generation of His-tagged proteins in *E. coli* in Doyle S A, Murphy M B, Massi J M, and Richardson P M (2002) High-Throughput Proteomics: A Flexible and Efficient Pipeline for Protein Production. *J. Proteome Research* December; 1(6):531-536, which is hereby incorporated by reference. In a preferred embodiment, Ni-NTA magnetic beads are used for the immobilization of His-tagged protein targets during selection.

In another embodiment, targets can be labeled with a tag such as biotin which permits the use of streptavidin-coated magnetic beads which are widely available, such as Streptavidin-coated DYNAL spheres M280 (Dynal Biotech, Inc., Lake Success, N.Y.). The target molecule can be easily linked or conjugated to streptavidin-coated magnetic beads due to the strong interaction between biotin and streptavidin.

The target-bound magnetic beads can be prepared by first equilibrating a slurry (approximately 45 μg capacity) of magnetic beads into a buffer preferably having a salt concentration of pH 7.0 to 8.0, preferably about pH 7.5. A suitable solvent, for example, is PBS-T (50 mM $K_2HPO_4$, pH 7.5, 150 mM NaCl, 0.05% TWEEN 20). The equilibrated beads should be resuspended in the buffer then purified target is added and mixed. The bead-bound target can then washed and diluted with buffer and stored at 4° C.

C. Library of Aptamer Sequences

In one aspect of the invention, a library of $10^8$ to $10^{15}$ random aptamers is first generated and incubated with the target molecule. In a preferred embodiment, the library should contain at least $6 \times 10^{14}$, preferably approximately $1 \times 10^{15}$ aptamer sequences. In a preferred embodiment, these aptamer sequences are comprised of degenerate oligonucleotide sequences about 20 to 50 base pairs in length, more preferably about 30 to 40 base pairs in length.

The aptamer sequences may further comprise fixed flanking sequences. In a preferred embodiment, the fixed flanking sequences are primer sequences flanking the degenerate oligonucleotide sequence on both ends. The primer sequences can be for use in downstream steps including, but not limited to, hybridization, replication, amplification, ligation and sequencing. In a preferred embodiment, the length of the entire aptamer sequence including the flanking fixed sequences is about 40 to 120 bases long, more preferably between 70-90 bases long, and most preferably between 75-85 bases long.

The entire aptamer sequence including the fixed sequences can be made using commercial oligonucleotide synthesis, with the degenerate portions of the aptamer sequences made preferably through completely random synthesis, but these degenerate sequences can also be made degenerate by creating specific degenerate sequences.

Any primer sequence suitable for PCR, cloning, sequencing and other downstream steps can be used as a flanking sequence. In one embodiment, the flanking sequences are primers for amplification. For example, primers such as 5'-GGTATTGAGGGTCGCATC-3' (SEQ ID NO: 17) and 5'-GATGGCTCTAACTCTCCTCT-3' (SEQ ID NO: 18), can be used. The entire aptamer sequence would be as follows: 5'-GGTATTGAGGGTCGCATC-N-GATG-GCTCTAACTCTCCTCT-3' (SEQ ID NO: 1), where N represents the degenerate sequence.

Primers that anneal to the 5' and 3' sequences flanking the degenerate region can also be used during selection and cloning. In a preferred embodiment, the flanking sequences are primers suitable for facilitating an improved cloning procedure in a vector that permits quick cloning such as ligation independent cloning (LIC). Ligation independent cloning (LIC) refers to a cloning procedure that does not require restriction enzymes, DNA ligase, or alkaline phosphatase. The 5' ends of the primers used to generate the clonable PCR fragments contain an additional sequence (of about 12 nt) lacking dCTP. As a result, the amplification products include 12 nt sequences lacking dGTP at their 3' ends. The 3' terminal sequence can be removed by the action of the 3'→5' exonuclease activity of T4 DNA polymerase in the presence of dGTP, leading to fragments with 5' extending single stranded (ss) tails of a defined sequence and length. Similarly, the entire plasmid vector is amplified with primers homologous to sequences in the multiple cloning site. The vector oligos have additional 12 nt tails complementary to the tails used for fragment amplification, permitting the creation of ss-ends with T4 DNA polymerase in the presence of dCTP. Circularization can occur between vector molecules and PCR fragments as mediated by the 12-nt tails, but not in mixtures without insert fragments. See, Aslandis and dejong, *Nucleic Acids Research* 18:6069-6074 (1990). Examples of preferred flanking sequences for LIC are: "LIC-F": 5'-GGTAT-TGAGGGTCGCATC-3' (SEQ ID NO: 2) and "LIC-R": 5'-AGAGGAGAGTTAGAGCCATC-3' (SEQ ID NO: 3) in biotinylated and non-biotinylated forms (HPLC purified, QIAGEN Operon, Alameda, Calif.).

III. Optimization of Method for High-Throughput Selection

A. Interacting the Target with the Aptamer Library

In the initial round of selection, the library should be incubated with the bead-bound target to produce bead-target-aptamer sequence complexes. In this step it is helpful to use at least a 10-fold molar excess of ssDNA in a volume to a 10 nM concentration of the target molecule, however, it may not be necessary. A preferred solution and protocol for interacting the library with the bead-bound target is the following: 1 nmol of the library is diluted into 100 µL of a buffer in a tube and heated to 95° C. for 2 min then immediately cooled at 4° C. This material was added to 10 mL of PBS-T containing 1 µg/mL BSA, 0.1 µg/mL dIdC. 100 pmol of bead-bound target is then added to this mixture and incubated with rotation for 30 min at room temperature.

B. Stringency of Interaction Conditions

The interaction conditions will affect the affinity of the aptamers selected. Therefore, the aptamer library should interact with the target molecule at a concentration preferably at or below the desired affinity. For example, if affinity of $10^{-6}$ M or higher is desired, the concentration of the target molecule is preferably at or below $10^{-6}$ M. The selection stringency can be adjusted by choosing the appropriate binding and washing conditions as is known in the art. For example, the selection stringency can be manipulated with salt concentrations between 50 mM and 250 mM NaCl or preferably between 100 mM and 200 mM NaCl. The inventions also contemplates that the selection stringency can be adjusted by varying the amount of binding time, wash volumes, magnesium or cation concentrations, or the concentration of target or library sequences present.

After allowing the aptamer library to interact with the magnetic bead bound-target molecule preferably as mixture in a vessel, magnetic force is applied to the mixture to separate bead-target-aptamer sequence complexes from unbound aptamer sequences.

C. Releasing and Amplifying Selected Aptamers

In one embodiment, the mixture in the vessel is subject to a magnetic field and magnetic beads are retained on the side of the tube while unbound aptamers can be washed away with buffer. The washing procedure is repeated several times under either the same or more stringent conditions applied to the bead-target-aptamer sequence complexes to select for higher affinity aptamers. Once the supernatant is removed, the bead-target-aptamer sequence complexes and magnetic beads can be washed with buffer. The aptamers bound to the target can be eluted and then subjected to PCR amplification using primers that are complementary to the flanking ends of the aptamer sequence. Elution is preferably done by resuspending the bead-target-aptamer sequence complexes in buffer compositions. For example, 10 ul 20 mM Tris, 500 mM imidazole, pH 7.5.

PCR amplification of the aptamer sequence is preferably performed using a forward primer and a biotinylated reverse primer conplementary to the flanking ends to facilitate separation of the DNA strands after amplification. For example, 1 µM primers "LIC-F" (SEQ ID NO: 2) and biotinylated "LIC-R" (SEQ ID NO: 3) were used in Example 1. Using these primers will generate PCR products with a biotin moiety attached to the non-aptamer strand. Single-stranded aptamers (non-biotinylated strand) are then separated from the complementary strand and addition of a magnet to capture the biotinylated non-aptamer strand. Separation of the single-stranded aptamers from the complimentary strand can be carried out by incubation with heat, or more preferably, incubation with a strong base, such as NaOH. After separation, the ssDNA aptamers are removed in the supernatant and diluted. Finally, the single-stranded aptamers are heated for several minutes then immediately placed at 4° C. until the next round of selection.

In order to remove aptamers that bind to the magnetic beads and not the target, counter-selection should be performed after several rounds. Counter-selection is done without any target present to remove any aptamers that might bind to the beads alone.

D. Optimization of Selection Cycles

In a preferred embodiment, the enrichment of aptamers that bind a particular protein of choice should be performed for a sufficient number of cycles. The enrichment of the aptamers should be monitored after at least 5, 10, and 15 rounds of selection for enrichment. Satisfactory enrichment should be accomplished within 10 to 15 cycles of selection (See FIGS. 6 and 8).

For additional rounds of selection, the amount of protein is recommended to be reduced by about half, in rounds 2-10, and subsequently in half again for rounds 11-15, and so on. Reduction in the incubation time is also recommended. After round 2, the PCR cycle number should also be reduced, preferably to 10 cycles, because of the increased likelihood of amplification of products of incorrect size. More than 15 cycles of amplification may lead to the production of larger fragments, and later identified as concatamers.

In one embodiment, 15 rounds of selection should produce high affinity aptamers using manual or high-throughput processing. The throughput of the present method is approximately 32 aptamers per month and amenable to a multi-well high throughput approach which may be scaled-up to produce about 384 aptamers per month.

IV. Further Amplification of Isolated Aptamers

The enriched aptamer sequence that binds to the target molecule of interest can be cloned into an appropriate vector for further amplification and sequencing.

After sufficient number of rounds to complete enrichment, the single-stranded aptamer sequences should be amplified by PCR and the PCR products concentrated and purified. In one embodiment, the PCR primer sequences are primers complementary to the flanking sequences in the aptamer sequences. The purified aptamer sequences can then be cloned into a vector, and transformed into E. coli. A sufficient number of colonies are picked for each sample, and the isolated plasmids are amplified and then sequenced.

Exemplary plasmids and vectors that can be used for cloning include, but are not limited to, LIC vectors such as pUC18LIC and pET30XaLIC.

The amplification of the cloned aptamer sequence before sequencing can be done by rolling circle amplification or by traditional concentration and purification using such commercially available kits as a 96-well mini-prep (Qiagen, Valencia, Calif.). However, the rolling circle amplification system may be more preferred in some cases because it is easier, more efficient and cost-effective. The cloned aptamer sequence can be then sequenced by known sequencing means such as using a T7 promoter primer in the Big-dye Terminator kit (Qiagen, Valencia, Calif.) and run on a sequencer.

Sequences can be analyzed and aligned using such programs as CLUSTALX v. 1.81 (Higgins D G, Sharp P M. (1988) *Gene* December 15; 73(1):237-44)) or other alignment programs. Pattern analysis is suggested to be performed using a program such as CONSENSUS (G. Z. Hertz and G. D. Stormo. (1995) *Proceedings of the Third International Conference on Bioinformatics and Genome Research* 201-216).

V. Evaluating Isolated Aptamers for Binding Activity

The term "binding activity" is herein meant to describe the measure of the strength of the binding or affinity of molecules to each other. The functional binding activity of aptamers selected by the method of the invention can be illustrated in several assays. These assays should determine the dissociation constant ($K_D$), which is a measure of the strength of binding activity or affinity between the isolated aptamers and the target molecules. As is known in the art, a low dissociation constant indicates stronger binding and affinity of the molecules to each other. Therefore, a preferred dissociation constant should be at least $10^{-4}$M, more preferably at least $10^{-6}$M, most preferably at least $10^{-8}$ and $10^{-9}$M.

Enzyme-linked assays provide a means of quickly evaluating a group of aptamers from a selection by measuring their relative affinities, and this kind of triage can be used to prioritize aptamers for more detailed characterization See Drolet D W, Moon-McDermott L, Romig T S. (1996) An enzyme-linked oligonucleotide assay. *Nat. Biotechnol.* August; 14(8): 1021-5, which describes the assay and is hereby incorporated by reference. Enzyme-linked assays can also provide information about cross-reactivity. Enzyme-linked assays offer advantages over other techniques, such as equilibrium dialysis and electrophoretic-mobility shift assays that are conventionally used to evaluate aptamers from a selection. These advantages include the lack of radioisotope usage, increased throughput in a multi-well plate, minimization of waste, and ease of precise quantitation of the relative binding affinities.

Using aptamers in a protein blot analysis is another means of characterizing their specificity. For example, the TTF1 Aptamers A and C selected for in Example 1 were tested by chemiluminescent protein blot analysis, however only the TTF1 AptamerA worked in this application suggesting that, just as some antibodies fail to recognize the denatured form of a protein, some aptamers will recognize epitopes that are absent in the denatured form of the protein. The TTF1 aptamer showed no cross-reactivity to *E. coli* proteins in a cleared lysate on the blot and was similar in specificity observed for the anti-PentaHis-HRP antibody.

Lastly, the binding activity of the aptamers of the invention can be analyzed through surface plasmon resonance (SPR). The SPR technique is an optical method for measuring the refractive index of materials adsorbed on a metal, such as the difference between the refractive index of a buffer (i.e. water) and the refractive index of a molecule bound to the surface. Examples of SPR platforms to perform SPR include include but are not limited to those available from Applied Biosystems (Foster City, Calif.) and Biacore Inc. (Piscataway, N.J.).

VI. Utility of Selected Aptamers

The aptamers isolated by the methods described by the invention can be used as affinity ligands to separate and purify target molecules, as probes to trace, monitor, detect and quantitate target molecules, or to block, allow, activate or catalyze reactions that are physiologically relevant to achieve therapeutic effect. Aptamers so isolated have utilities similar to antibodies. They can act as a pharmaceutical agent, bind to a specific target and direct specific molecules to a desired site, and/or they can inhibit or promote a physiologically relevant reaction to achieve a desired therapeutic effect. Various in vivo, ex vivo, and in vitro methods can employ aptamers isolated by methods described herein, as will appreciated by one of skill in the art.

Within respect to in vitro procedures, aptamers can be used in affinity purification matrixes to purify target molecules. The subject aptamers are ideal for chromatographic separations of target molecules from contaminants and for purifying target protein molecules from cell cultures or cell extracts. The immediate application of these aptamers is to purify antibodies, enzymes, hormones, receptors, and factors that are used in research, development, diagnostic, pharmaceutical, industry applications.

In one embodiment, the key function of high affinity aptamers in applications such as protein purification, protein profiling chips, surface plasmon resonance and diagnostics is to recognize and separate the target protein from a complex mixture of proteins.

Also described herein is the successful application of aptamer affinity chromatography for one-step purification of a protein from the complex mixture of proteins in the soluble fraction of bacterial cell lysates. Although aptamer affinity chromatography has been described and demonstrated for the purification of a protein from conditioned cell culture media, this purification technique has not been previously demonstrated for more complex samples such as cell cultures and serum. Detrimental effects from DNase activity in purification from bacterial lysates were not observed using the aptamers isolated by the method described herein, unlike the problems associated with DNase degradation of aptamers that occurs when purifying targets from serum (Romig T S, Bell C, Drolet D W. (1999) Aptamer affinity chromatography: combinatorial chemistry applied to protein purification. *J Chromatogr B Biomed Sci Appl*. August 20; 731(2):275-84). Importantly, aptamer affinity chromatography provides a means of protein purification of the native form of a protein without relying on affinity tags that may adversely affect protein structure, function or ability to form crystals for structural characterization.

Selected aptamers having specific chiral properties can be used to separate chiral compounds and obtain optically pure chemicals. They can also be used in place of antibodies in various research, development and diagnostic applications such as blotting techniques, flow cytometry, immunoassays, strip assays, immunohistological techniques, affinity sensors, etc. Aptamers selected by this methods can further be used to monitor, trace, detect and quantitative desired target such as proteins, antibodies, microbes, virus, bacteria, macromolecules, and small molecules and used as valuable tools for proteomics studies of protein and their function.

In addition, the Examples fully demonstrate the abilities of aptamers generated by the method to bind their target protein with high affinity and specificity, and detail their uses in a number of assays. It is also further contemplated that one could use a pool of aptamers in a given application; for example, a mixture of 6H5 (SEQ ID NO: 14), 6H1 (SEQ ID NO: 15) and/or 6H7 (SEQ ID NO: 16).

Herein described are a series of aptamers which bind to a polyhistidine sequence coupled to various proteins and used in many applications including as protein purification reagents. These His6 aptamers isolated are useful for the capture and detection of target molecules that contain or are fused to polyhistidine residues (His6). The use of a His6 tag for identification, detection, purification and manipulation of proteins and other target molecules is well known in the art. Therefore, aptamers that bind or detect His6 tags may be useful in many biological applications including, but not limited to, affinity resins, magnetic or polymer beads, as a diagnostic detection reagent, to capture or immobilize reagents for diagnostic, detection or quantitative studies.

In a preferred embodiment, the aptamer sequences used to bind to His6 affinity tags have at least 80% homology, more preferably 90%, and more preferably at least 95% homology to the degenerate aptamer sequences of SEQ ID NOS: 14, 15 and 16. The present aptamers can be flanked by primer sequences, such as the primers of SEQ ID NO: 17 and SEQ ID NO: 18 as described herein. It is contemplated that these aptamer sequences may be varied in the degenerate sequence region, by up to 20 percent, more preferably by 10 percent, most preferably by 5 percent, while retaining the functional properties as described herein.

One aspect of the present His6 aptamers is their application to solid supports. In one aspect, arrays of tagged proteins can be immobilized in an array on a solid support, in which the solid support has been spotted with an aptamer such as the aptamers of SEQ ID NOS: 14, 15 and 16. In another aspect, solid supports used in SPR may be modified to accept the present aptamers, and his-tagged proteins used as target molecules to be captured or immobilized by the present aptamers.

In one embodiment, the aptamer can be used as a capture agent to bind or immobilize a target protein to a solid support. The solid support can be any comprised of substrates having the structure and composition commonly associated with filters, wafers, wafer chips, membranes and thin films that one of ordinary skill in the art is aware of. However, it is contemplated that the solid support may be comprised of substrates including but not limited to resins, affinity resins, magnetic or polymer beads, or any a diagnostic detection reagent, to capture or immobilize reagents for diagnostic, detection or quantitative studies.

Further the solid supports may comprise any material depending on the desired use, including but not limited to glass, metal surfaces and materials such as steel, gold, silver, aluminum, copper, silicon, and glass, ceramic or polymeric materials such as polyethylene, polypropylene, polyamide, and polyvinylidenefluoride, etc. and combinations thereof. The solid support can be coated with any material to facilitate the attachment, binding, hybridization, immobilization or interaction of biological molecules on the surface. In one embodiment, the solid support is a glass slide having a layer of gold, carboxymethylation, dextran, collagen, avidin or streptavidin to support the attachment or interaction. A variety of molecules can then be attached to the solid support by means of this attachment or interaction. For example, if the support is coated with streptavidin, biotinylated oligonucleotides can be attached to the support by means of the strong interaction between biotin and streptavidin.

In this manner, the His6 aptamers of the invention can then be attached to the surface of the support through the layer of material coating the solid support. The term "attached to said solid support" herein is meant attached, removeably attached, bound, covalently bound, non-covalently bound, conjugated, hybridized, immobilized or interaction with the support surface; there may be any number of intervening layers or molecules between the aptamer and the solid support, that one of ordinary skill in the art will recognize depending on the intended use. For example, the aptamer can be attached to the support by means of an oligonucleotide that is covalently attached to the support on one end and then attached to the aptamer through base complementarity on the other end of the oligonucleotide.

It is also contemplated that arrays of the aptamers are attached to the solid supports. It is understood that the array may be as few as 2 aptamers or as many as 10,000,000 depending on the desired end use. It is further contemplated that arrays of the aptamers can be used to capture large amounts of a molecule or protein of interest from a sample. The captured and immobilized molecules will permit diagnostic, biological, qualitative and quantitative studies requiring immobilized or bound proteins, ligands, and peptides.

In one embodiment, as shown in FIG. 12B, the solid support is streptavidin-coated having a biotinylated His6 aptamer selected from SEQ ID NOS: 14, 15 and/or 16, attached to the support, thereby providing a surface that can capture and bind to any His6 tagged protein, ligand or peptide. The resulting support having immobilized His6 tagged proteins, ligands or peptides will permit diagnostic, biological, qualitative and quantitative studies requiring immobilized or bound target molecules. Furthermore, the His6 aptamer does not easily disassociate from solid support but remains firmly attached as shown in the Examples. Therefore, the immobilized target molecules should not be easily dissociated from the solid support upon binding the aptamer.

In another embodiment, as shown in FIG. 12C, the solid support is streptavidin-coated and attached to the support is a biotinylated oligonucleotide that binds to a fixed portion of at least one of the His6 aptamers of SEQ ID NOS: 14-16 by base complementarity. One with ordinary skill in the art would recognize how to design such an oligonucleotide using basic complementary nucleic acid bases, i.e. A-T and C-G. This would also provide a surface that can capture and bind to any His6 tagged proteins and peptides applied to the surface. The resulting support will permit diagnostic, biological, qualitative and quantitative studies requiring immobilized or bound proteins, ligands, and peptides. The added flexibility in this embodiment, is that the chip can be used with any His6 aptamer of the invention as well as the aptamers isolated using the methods described herein.

Supports having the aptamers attached thereto as described above are stable and can be stored for sufficiently longer periods of time than current available supports using antibodies as capture reagents because of the longer shelf-life of DNA and nucleic acids. As shown later in the Examples, the aptamers have equal or better ability to capture His6-tagged proteins, peptides or ligands. Furthermore, the aptamer or the proteins and ligands bound, can be removed from the solid support allowing the solid support to be reused with different binding pairs.

Example 1

Library Creation and Aptamer Selection

An improved protocol for DNA aptamer production that is relatively easy and scalable without the need for expensive robotics is described herein. Thyroid transcription factor 1 (TTF1), a well characterized member of the NK homeodomain transcription factors (See Harvey R P. (1996) NK-2 Homeobox Genes and Heart Development. *Developmental Biology*. 178, 203-216; and Ristoratore F, Spagnuolo A, Aniello F, Branno M, Fabbrini F, Di Lauro R. (1999) Expression and functional analysis of Cititf1, an ascidian NK-2 class gene, suggest its role in endoderm development. *Development*. November; 126(22):5149-59) was used as a target molecule. TTF1 is expressed in the developing thyroid, lung, and brain of vertebrates, and several effector genes have been identified in thyroid and lung tissues. The DNA recognition site of TTF1 differs from other homeodomain containing proteins, attributed to the NK-type homeodomain (Guazzi S, Price M, De Felice M, Damante G, Mattei M G, Di Lauro R. (1990) Thyroid nuclear factor 1 (TTF-1) contains a homeodomain and displays a novel DNA binding specificity. *EMBO J* November; 9(11):3631-9). Following 15 rounds of selection, the affinity and specificity of several aptamers were characterized, and their uses in assays were described for the capture and identification of proteins, such as Western blots, enzyme-linked assays, and affinity purification.

Cloning, protein expression, and purification. Thyroid transcription factor 1 (TTF1) was cloned from *Ciona intestinalis* 16 hour embryos following RNA isolation (Trizol reagent, Gibco, Carlsbad, Calif.) and first strand synthesis (Superscript First Strand Synthesis System for RTPCR, Gibco, Carlsbad, Calif.) by PCR using the following gene specific primers that contained 5' Ligation Independent Cloning (LIC) (Novagen, Madison, Wis.) compatible ends: Forward 5'-GGTATTGAGGGTCGCTCAGTTAGC-CCAAAGCATTCG-3' (SEQ ID NO: 19); Reverse 5'-AGAGGAGAGTTAGAGCCTTATCGGTAAA-CACTGTACAGGATCG-3' (SEQ ID NO: 20).

LIC was performed as previously described in Doyle S A, Murphy M B, Massi J M, and Richardson P M (2002) High-Throughput Proteomics: A Flexible and Efficient Pipeline for Protein Production. *J. Proteome Research* December; 1(6): 531-536), to insert the coding sequence of *Ciona intestinalis* TTF1 into the vector pNHis, which adds a hexahistidine tag to the amino-terminus of the encoded protein.

Subcloning. An expression vector was constructed from pET30 (Novagen, Madison, Wis.) by removing 117 bp 3' of the hexahistidine tag site that encoded extra affinity tags and by adding the sequence 5'TCCGGTAT-TGAGGGTCGCTCTAACTCTCCTCTG 3' (SEQ ID NO: 4) to allow for LIC cloning (FIG. 1). Construction of the LIC vector containing the N-terminal hexahistidine affinity tag is shown in FIG. 1. The new vector pNHis, encodes a protein with a N-terminal extension of 6 histidine residues followed by 6 additional amino acids that encode a factor Xa cleavage site. A stop codon was added to the gene sequence so that the 3' LIC sequence did not add 6 extra amino acids to the C-terminus of the protein sequence.

The new vector, pNHis, was linearized within the LIC sequence by digestion with BseR1, treated with mung bean nuclease to produce blunt ends, and gel purified. Cloning was performed as described in LIC cloning manuals (Novagen, Madison, Wis.). Briefly, the gene sequences were amplified by PCR using sequence specific primers with 5' adaptors (forward primer: 5' GGTATTGAGGGTCGC (SEQ ID NO: 5) and reverse primer: 5' AGAGGAGAGTTAGAGCCTTA (SEQ ID NO: 6)). The insert and vector DNA were treated with T4DNA polymerase in the presence of dGTP and dCTP, respectively, for 40 min. at room temperature (22° C.), and the polymerase was heat inactivated for 20 min. at 75° C. The fragments were annealed in a 10 min. reaction at room temperature, and transformed into NOVABLUE competent cells (Novagen, Madison, Wis.). Positive clones were confirmed by a colony PCR procedure using the T7 promoter (5' TAATACGACTCACTATAGGG 3' (SEQ ID NO: 7)) and T7 terminator (5' GCTAGTTATTGCTCAGCGG 3' (SEQ ID NO: 8)) primers, and confirmed by sequencing.

Two sources of coding sequence were used, the bacterium *Xylella fastidiosa*, and *Ciona intestinalis*, a primitive chordate. Eight randomly chosen *Xylella* proteins, ranging from 10 to 32 kDa were cloned into the expression vector. Five full-length *Ciona* proteins (42 to 88 kDa) were also cloned into this vector, as well as several gene fragments containing DNA binding domains.

Expression Screening. Expression constructs from *Xylella fastidiosa* and *Ciona intestinalis* were tested under various growth conditions using the dot blot procedure to identify optimal growth conditions for each protein (FIG. 2). Expression screen dot blots of *Xylella* and *Ciona* samples, grown for 4 hours or overnight (o/n) were analyzed to determine which samples should be chosen for further purification. The standard curve generated on each blot was reproducible and used to approximate the concentrations of protein in the sample spots. A good correlation between spot intensities and protein concentration was obtained (data not shown).

The High-throughput Protein Purification (96-well) protocol used to purify the proteins can be described briefly as follows: (1) Grow and lyse cultures in 24-well blocks, then pellet insoluble material by centrifugation. (2) Incubate clear lysate with Ni-NTA resin in batch. Combine 50 μl of 50% slurry Ni-NTA Superflow (Qiagen, Valencia, Calif.) with cleared lysate in 96-well filter plate (Genemate) and mix at 4° C. for 20 min. (3) Wash wells 3× with 750 μl wash buffer on vacuum manifold. (4) Elute proteins into 96-well microtiter plate on vacuum manifold. Add 100 µl elution buffer (containing imidazole and 10% glycerol), incubate 5 min, and apply vacuum.

Plasmids encoding *Xylella* genes were transformed into BL21 (DE3) Gold cells (Stratagene, La Jolla, Calif.) and plasmids encoding *Ciona* genes were transformed into Rosetta pLysS cells (Novagen, Madison, Wis.) based on previous experiments. Initial starter cultures grown at 37° C. were used to inoculate 5 ml LB medium containing 50 μg/ml kanamycin in 24-well blocks. Once an $O.D_{600}$ of 0.6 to 0.8 was reached, the cultures were induced with IPTG at a concentration of 0.1 mM or 1.0 mM, and grown at various temperatures (18° C., 25° C., 30° C. and 37° C.) for 4 hours or overnight. In the present study only temperature, and induction strength and time were tested, however, many other conditions (growth medium, host cells) can be added to the screen.

The cells were harvested by centrifugation, frozen at −70° C., then thawed and resuspended in 0.5 ml lysis buffer (50 mM $NaH_2PO_4$, 300 mM NaCl, 2 mM $MgCl_2$, 20 mM imidazole, pH 8.0) containing 1 mg/ml lysozyme, 0.5 μl (12U) Benzonase nuclease (Novagen, Madison, Wis.), and 2 μl protease inhibitor cocktail (Sigma, St. Louis, Mo.). Following incubation on a plate shaker at 4° C. for 30 min, an aliquot of crude lysate was removed, and the remainder of the sample was clarified by centrifugation.

Two μl of crude and cleared lysate were spotted on Protran nitrocellulose membrane (Schleicher and Schuell, Keene, N.H.) using a 12-channel pipette. A serial dilution of protein standard was also spotted (15-1500 ng of a 42 kDa protein). The membrane was incubated using the Western Processor developing system (Biorad, Hercules, Calif.) as follows: TBS (6 mM Tris-Cl, 150 mM NaCl, pH 7.5), 5 min, 3 cycles; blocking buffer (TBS with 3% BSA) 30 min; TBS T/T (TBS with 0.05% Tween 20 and 0.2% Tritin X-100), 5 min., 3 cycles; PentaHis HRP conjugate (Qiagen, Valencia, Calif.) (1:1000 in blocking buffer) 30 min.; TBS T/T, 5 min., 5 cycles. The membrane was then treated with metal-enhanced DAB substrate (Pierce) following the manufacturer's protocol, and scanned using a flatbed scanner. The blotting procedure was completed in less than 2 hours.

Overall, the *Xylella fastidiosa* proteins showed good total expression levels, with nearly all of the crude lysate samples exhibiting high intensity spots (data not shown). Two samples (proteins XF0233 and XF2614) showed little difference in the total protein and soluble protein samples under all conditions tested, indicating that these proteins are very soluble. For the remainder of the samples, however, a trend was seen where the solubility was increased with reduced growth temperature (≦25° C.). In addition, overnight induction conditions produced better protein yields than 4 hour induction conditions. Nearly identical results were obtained when samples were induced with 0.1 and 1.0 mM IPTG (data not shown).

The total expression levels for the *Ciona intestinalis* samples were not as consistent as in the *Xylella* set. Unlike the *Xylella* proteins, total expression was better in samples induced for 4 hours than overnight, although not at every temperature tested. Snail and TTF-1 expressed soluble protein under most conditions, while the remainder of the proteins showed reduced solubility when induced overnight. In the 4 hour samples, snail and TTF-1 produced their highest soluble yields at ≧25° C., where 25, 30 and 37° C. were roughly equivalent. For the proteins showing lower expression levels, no clear pattern was seen. Hox1 produced more soluble protein at ≧25° C., with the highest yield at 37° C., while Tbx2/3 and Tbx6 produced the highest yields of soluble protein at 30° C. These differences are probably due to the inherent stability of these proteins when expressed in bacteria. As with the *Xylella* samples, nearly identical results were obtained when the same experiments were performed with 0.1 and 1.0 mM IPTG induction (data not shown).

Significant differences were seen in the expression of full-length and DNA binding domains of *Ciona* proteins Tbx6 and Tbx2/3. The domain of Tbx6 showed little or no expression under any conditions, unlike the full-length protein, which expressed fairly well at higher temperature for 4 hours. The TBX2/3 domain (Tbx2/3d) clearly showed highest yields at ≦25° C., while the full-length protein expressed more soluble protein at ≧25° C. These results suggested that the cloned DNA fragments do not contain structurally stable DNA binding domains, and thus the smaller protein products were less stable than the full-length proteins. Comparison of additional full-length proteins and fragments will provide useful information regarding the ability of protein fragments containing specific domain motifs to fold into stable protein products when expressed in bacteria.

This expression screen allows for the identification of optimal conditions for soluble protein expression in a convenient and reproducible manner. The use of 24-well blocks in standard incubators for cell growth, standard lysis procedures, and simple centrifugation and sample spotting steps make it easily implemented, without the need for expensive robotics. In many cases, protein expression levels are sufficiently high to allow for direct purification of micrograms of protein from 5 or 10 ml cultures grown in the 24-well blocks. Alternatively, if more protein is required, the optimal conditions for scaled up experiments can be identified using this method.

After screening several expression conditions, TTF1 was found to be most highly expressed in Rosetta (DE3) pLysS cells (Novagen, Madison, Wis.) induced with 1.0 mM IPTG at 37° C. for 4 hours. One liter of culture grown under these conditions was harvested by centrifugation at 5,000×g for 10 min at 4° C. The pellet was resuspended in 30 mL of resuspension buffer (50 mM $Na_2HPO_4$, 300 mM NaCl, 20 mM imidazole, 0.1% Triton X100, 5 mM 2-mercaptoethanol at pH 7.0 with 1 mM PMSF Plus (Roche-Applied-Science, Indianapolis, Ind.), and 1× Protease Inhibitor Cocktail (Sigma Chemicals, St. Louis, Mo.)). The cells were then lysed with the Emulsiflex-C5 (Avestin, Ottawa, Ontario, Canada) homogenizer at 15,000 psi. The lysate was centrifuged at 15,000×g for 25 min at 4° C. to remove insoluble material. Chelating Sepharose High Performance resin (Amersham Biosciences, Piscataway, N.J.) was charged with 0.1 M $NiSO_4$ and washed with 10 column volumes of sterile water. The cleared lysate was incubated with 300 μL of 50% slurry of $Ni^{+2}$ charged resin and bound in batch for 20 min with constant rotation then loaded onto an empty polypropylene column (Qiagen, Valencia, Calif.) and allowed to drain by gravity flow. The 150 μL column was then washed with 50 column volumes of resuspension buffer containing 20% glycerol and the bound proteins were eluted with 0.5 column volumes of elution buffer (1 M imidazole, 50 mM $Na_2HPO_4$, pH 7.0, 150 mM NaCl, 0.1% Triton-X100, 20% glycerol, and 5 mM 2-mercaptoethanol).

Determination of Protein Yield and Purity. The concentration and purity were determined using 4 μL in a Protein 200 LABCHIP kit (Caliper, Newton, Mass.) run on an Agilent 2100 Bioanalyzer (Agilent Technologies, Palo Alto, Calif.). The protein LABCHIP was prepared by injecting 12 μl of a gel matrix and fluorescent dye mixture into the chip using a chip priming station. The samples were prepared by mixing 4 μl of protein and 2 μl of a SDS-based denaturing sample buffer containing β-mercaptoethanol as well as an upper and lower mass standard and by boiling the mixture. Samples and ladder were then diluted to 90 μl with water and 6 μl of each diluted sample was loaded into a well of the LABCHIP. Dilution of the samples is necessary to decrease background fluorescence due to the SDS in the sample buffer. The LABCHIP was then placed in an Agilent 2100 Bioanalyzer, and electrophoresed for 30 minutes. Agilent Biosizing software was used to determine the size of the proteins of interest by normalization against two internal standards of 6 and 210 kDa. The fluorescent peak identification settings were adjusted for sensitivity, 0.8 for the minimum peak height, 0.2 seconds for the minimum peak width, and 4 for the slope threshold.

In vitro selection of aptamers. A degenerate oligonucleotide library was synthesized at 1 μmole scale and HPLC purified (QIAGEN Operon, Alameda, Calif.). This material was diluted to 0.1 nmol/μL in 10 mM Tris, pH 8, and stored at −20° C. This library, referred to in this example as "LIC-Apt", is composed of 40 random nucleotides flanked by sequences suitable for ligation independent cloning (LIC): 5'-GGTATTGAGGGTCGCATC-3' (SEQ ID NO: 17) and 5'-GATGGCTCTAACTCTCCTCT-3' (SEQ ID NO: 18).

Primers that anneal to the 5' and 3' sequences flanking the degenerate region of LIC-Apt that were used during the selection and cloning were: "LIC-F": 5'-GGTATTGAGGGTCGCATC-3' (SEQ ID NO: 2); "LIC-R": 5'-AGAGGAGAGTTAGAGCCATC-3' (SEQ ID NO: 3); in biotinylated and non-biotinylated forms (HPLC purified, QIAGEN Operon, Alameda, Calif.).

Protein-bound Ni-NTA magnetic beads were prepared by first equilibrating 150 μL of a 5% slurry (approximately 45 μg capacity) of Ni-NTA magnetic beads (Qiagen, Valencia, Calif.) into PBS-T (50 mM K$_2$HPO$_4$, pH 7.5, 150 mM NaCl, 0.05% Tween 20). The equilibrated beads were resuspended in 1250 μL of PBS-T and 25 μL of 2 mg/mL purified TTF1 was added (a 1:50 dilution to lower the imidazole concentration) and mixed with rotation for 30 min at 4° C. The bead-bound TTF1 was then washed 3× with 1 mL PBS-T, and diluted to 0.25 μg/μL (5 pmol/μL of 50 kDa TTF1) with PBS-T and stored at 4° C.

In the initial round of selection, the "LIC-Apt" library was incubated with the bead-bound TTF1 using a 10-fold molar excess of ssDNA in a volume that gave a 10 nM TTF1 concentration. 1 nmol of "LIC-Apt" was diluted into 100 μL of PBS-T in a PCR tube and heated to 95° C. for 2 min then immediately cooled at 4° C. This material was added to 10 mL of PBS-T containing 1 μg/mL BSA, 0.1 μg/mL dIdC. 100 pmol of bead-bound TTF1 was then added to this mixture and incubated with rotation for 30 min at room temperature. The tubes were then applied to a magnet (Dexter Magnetics, Elk Grove Village, Ill.), the supernatant removed, and the beads were washed 3× with 1 mL PBS-T, mixing by inversion for each wash step. The proteins and bound aptamers were eluted from the Ni-NTA magnetic beads with 10 μL of 20 mM Tris, pH 7.5, 500 mM imidazole and transferred to PCR tubes. 100 μL PCR reactions contained 1.25 units Pfx polymerase (Invitrogen, Carlsbad, Calif.), 1 μM primers "LIC-F" and biotinylated "LIC-R", 0.1 mM dNTPs, 0.5 mM MgSO$_4$, and 0.1× enhancer solution. Amplification conditions were 2 min at 95° C.; 15 cycles: 30 sec at 95° C.; 30 sec at 56° C.; 30 sec at 68° C.; 2 min at 68° C. This protocol produced 2-5 μg of the correct size product as determined using a DNA 500 lab-chip (Caliper, Newton, Mass.) on an Agilent 2100 Bioanalyzer. After the amplification step, 90 μL of the PCR product and 23 μL 5M NaCl were then mixed with 1 mg of M-280 streptavidin magnetic beads (Dynal Biotech, Brown Deer, Wis.) for 10 min at room temperature, then washed 3×1 mL with PBS-T. Single-stranded aptamers (non-biotinylated strand) were separated from the immobilized complementary strand using a 5 min incubation of 50 μL of fresh 100 mM NaOH. The tubes were applied to a magnet and the ssDNA was removed and diluted into 1 mL PBS-T, containing 10 μL of 100 mM monobasic phosphate buffer to adjust the pH to 7.5. Finally, the material was heated to 95° C. for 2 min then immediately placed at 4° C. until the next round of selection.

For additional rounds of selection, the amount of protein was reduced to 50 pmol (rounds 2-10), and subsequently 25 pmol (rounds 11-15) in a binding volume of 1 mL, and the incubation time was reduced to 10 min. After round 2, the PCR cycle number was reduced to 10 cycles because of the amplification of products of incorrect size. More than 15 cycles of amplification often led to the production of larger fragments, later identified as concatamers. In order to remove aptamers that bind to the Ni-NTA magnetic beads, counter-selection was performed after rounds 3, 6, 9, and 12. A 20 μL aliquot of a 5% slurry of Ni-NTA-magnetic beads was added to the 1 mL of ssDNA in PBS-T and incubated for 10 min with rotation, then applied to a magnet and the supernatant removed for the next round.

After round 15, the material was amplified by PCR with "LIC-F" and "LIC-R" primers, and the products were purified with MinElute (Qiagen, Valencia, Calif.), LIC-cloned into pET30XaLIC vector (Novagen, Madison, Wis.), and transformed into NovaBlue *E. coli* (Novagen, Madison, Wis.). 32 colonies were picked for each sample, and the plasmids purified by 96-well mini-prep (Qiagen, Valencia, Calif.). The plasmids were sequenced using a T7 promoter primer in the BIG_DYE Terminator kit and run on an ABI 3730 Sequencer (Applied Biosystems, Foster City, Calif.). Sequences were aligned using ClustalX v. 1.81 (Higgins D G, Sharp P M. (1988) CLUSTAL: a package for performing multiple sequence alignment on a microcomputer. *Gene* December 15; 73(1):237-44). Pattern analysis was performed using CONSENSUS (G. Z. Hertz and G. D. Stormo. (1995) Identification of consensus patterns in unaligned DNA and protein sequences: a large-deviation statistical basis for penalizing gaps. *Proceedings of the Third International Conference on Bioinformatics and Genome Research* 201-216).

Five groups of identical sequences were identified after the 15 rounds of selection, including one aptamer "A" that represented 30% of the total evaluated. Thus, the selection conditions using magnetic beads were sufficiently stringent for successful enrichment in 15 rounds. The degenerate portions of the aptamers isolated are listed as follows:

```
TTF1 Aptamer A
SEQ ID NO: 9
TCAAAAGGGGTGATTGCTTGCACAATGACAGGGTAGGACA

TTF1 Aptamer B
SEQ ID NO: 10
GATACACGGGCGGAGGAGGTGGGGGGGGTAGGTGGGTAT

TTF1 Aptamer C
SEQ ID NO: 11
TGGCTAGTGGGTAAGGGGCGGGAGGGTGACAGGGCGATCC

TTF1 Aptamer D
SEQ ID NO: 12
TTATGGGGATGAAAGTGGTGTTCGGGTTCGCCACTTCCAC

TTF1 Aptamer E
SEQ ID NO: 13
TTGGGGTGGGAGGGCGGGTTAACAAAGATAGCGCAACAGG
```

The aptamers that were generated (FIG. 4) did not have affinity towards the Ni-NTA magnetic beads (not shown).

Interestingly, there were 2 aptamers—TTF1 AptamerA and TTF1 AptamerC—that contained a consensus sequence (FIG. 4), although this consensus may not necessarily be responsible for the affinity towards TTF1 since all the aptamer sequences obtained displayed affinity towards the protein (not shown). In addition, several G repeats were found in each group. The TTF1 dsDNA binding consensus sequence (5' T(C/T)AAGTG 3') is not contained in any of the aptamer sequences. In addition to the aptamers described in FIG. 4, there were 3 sequences that were each represented as singletons (not shown).

Example 2

Determination of the Specificity of a TTF1 Aptamer

We used an enzyme-linked assay in order to prioritize the aptamers from the TTF1 selection for further characterization (not shown). This assay provided a rapid assessment of the relative binding capabilities of many aptamers from a particular selection experiment. The results suggested that TTF1 AptamerA may have the highest affinity for TTF1 (later confirmed by kinetic studies) and thus was chosen for further characterization. In addition, the enzyme-linked assay was used to provide information regarding cross-reactivity (FIG. 5). Employing a calorimetric detection system (Turbo-TMB+ sulfuric acid) for peroxidase activity conjugated to streptavidin, we observed a significant (100×) signal over background, and the data for triplicate samples ranged from 0.006+/−0.0002 to 0.63+/−0.05 absorbance units. In order to determine if the TTF1 aptamer "A" would recognize another homeodomain family member, the enzyme-linked assay was used to show that the TTF1 AptamerA does not cross-react with the homeodomain of HOX4 (FIG. 5), nor did the aptamer bind BSA. In addition, an aptamer that was selected for HOX4 binding (not described here) did not cross-react with the TTF1 protein.

Aptamer-enzyme linked assay. To measure the binding of aptamers to proteins immobilized on microtiter plates, 500 ng of purified TTF1 or purified HOX4 fragment was bound to wells of a Ni-NTA HisSorb plate (Qiagen, Valencia, Calif.) in 200 µL PBS-T for 2 hours at room temperature. The wells were then washed 3× with 200 µL PBS-T. Biotinylated aptamers (QIAGEN Operon, Alameda, Calif.) were diluted to 1 ng/µL in 200 µL PBS-T, heated to 95° C. and then cooled quickly to 4° C. 200 µL of aptamer was incubated with proteins in the HisSorb plate overnight at 4° C. on a plate vortex shaking gently. The wells were washed 4× with 200 µL PBS-T for 5 min each on a plate vortex. Streptavidin-HRP (Molecular Probes, Eugene, Oreg.) was diluted 1: 10,000 into PBS-T and a 200 µL aliquot was incubated with the proteins and bound aptamers in the HisSorb plate for 30 min at room temperature. The wells were washed again as described above, then 150 µL of Turbo-TMB (Pierce Biotechnology, Rockford, Ill.) was added to each well and incubated for 20 min at room temperature in the dark. The reactions were stopped with the addition of 150 µL of 1 M $H_2SO_4$ and the protein bound aptamer-streptavidin complex was quantified by determining the absorbance at 450 nm using a SpectraMax Plus (Molecular Devices, Sunnyvale, Calif.).

Example 3

Determination of the Affinity of Aptamers for TTF1

Figure 6:
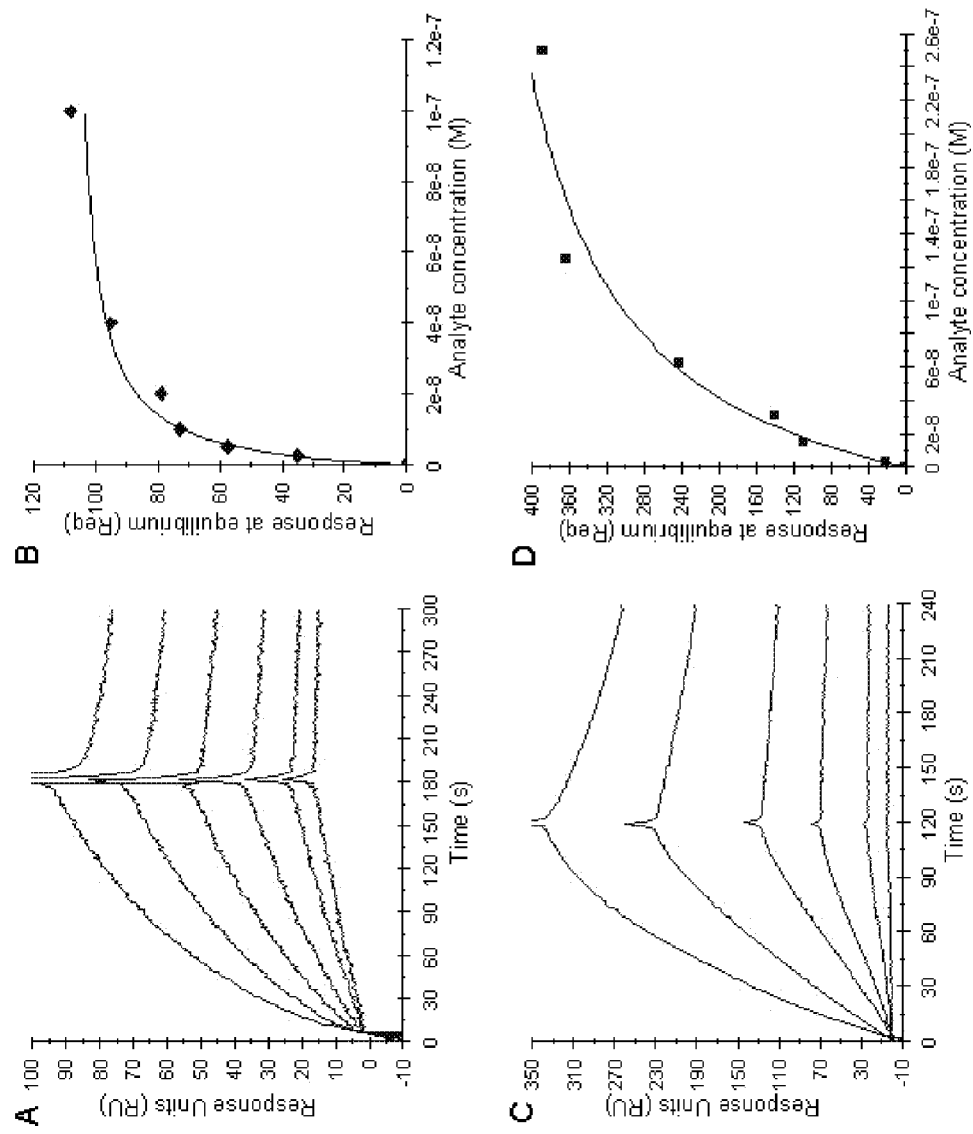
FIG. 6 comprises four graphs showing the determination of the affinities of aptamers for TTF1 using surface plasmon resonance. (A) Sensorgrams of the binding response to aptamer "A" measured for concentrations of 2.5, 5, 10, 20, 40, 100 nM TTF1 analyte. The $K_D=3.36\times10-9$ M as determined from a global fit of the kinetic simultaneous $k_a/k_d$ model, assuming Langmuir (1:1) binding, and $Chi^2=14.1$. (B) Plot of the steady-state affinity for "A" using the Req values derived from sensorgrams in (A) fitted locally. The $K_D=5.14\times10-9$ M as determined from the steady state affinity model. (C) Sensorgrams of the binding responses to aptamer "C" measured for concentrations of 3, 12, 31, 62.5, 125, 250 nM TTF1 analyte. The $K_D=3.25\times10-8$ M as determined from a global fit of the kinetic simultaneous $k_a/k_d$ model, assuming Langmuir (1:1) binding, and $Chi^2=10.9$. (D) Plot of the steady-state affinity for "C" using the Req values derived from sensorgrams in (C) fitted locally. The $K_D=6.56\times10-8$ M as determined from the steady state affinity model.

We utilized surface plasmon resonance employing a BIAcore X instrument to measure the affinity of the interaction of TTF1 with aptamers immobilized on a sensor chip. Sensorgrams of a concentration series of TTF1 injected over TTF1 AptamerA or TTF1 AptamerC are shown in FIGS. 6A and C, respectively. The affinity, as described by the $K_D$, was determined by a global fit using the kinetic simultaneous $k_a/k_d$ model, assuming Langmuir (1:1) binding. The $K_D$ of TTF1 AptamerA for TTF1 was $3.36 \times 10^{-9}$ M, and the $K_D$ of TTF1 AptamerC for TTF1 was $3.25 \times 10^{-8}$ M. The steady state affinities of TTF1 for the aptamers, determined from plots of Req values derived from sensorgrams in (FIGS. 6A and C) fitted locally, correlated well with the simultaneous $k_a/k_d$ model (FIGS. 6 B and D). $K_D$ values for the remaining aptamer sequences (TTF1 Aptamers B, D, E) and the 3 singletons showed that these aptamers also displayed affinity towards TTF1, ranging from $2.2 \times 10^{-8}$ M to $6.7 \times 10^{-8}$ M (not shown).

BIAcore surface plasmon resonance. The affinity of the aptamers for their protein targets was measured using surface plasmon resonance (SPR) with a BIAcore X instrument (BIAcore, Piscataway, N.J.). Biotinylated aptamer (QIAGEN Operon, Alameda, Calif.) was diluted to 0.5 ng/µL in HBS-P (10 mM HEPES, pH 7.5, 150 mM NaCl, 0.05% Tween 20), heated to 95° C., and rapidly cooled at 4° C. before use. Approximately 100 RU of biotinylated aptamer (ligand) was immobilized to one flow cell of a streptavidin coated sensor chip. Purified TTF1 protein was diluted into HBS-P to give a series of concentrations of TTF1 protein (3, 12, 31, 62, 125, 250 nM or 2.5, 5, 10, 20, 40, 100 nM) that were injected over the surface for 2 min at a flow rate of 20 µL/min (to minimize mass transfer limitations). Bulk shift and non-specific interactions with the streptavidin were subtracted using the response from a reference flow cell. After measuring the off rates for 2 min for each analyte injection, complete regeneration of the surface was achieved with two 30 sec. injections of 0.05% SDS at 50 µL/min. The affinity, as described by the equilibrium dissociation constant ($K_D$), was determined globally by fitting to the kinetic simultaneous $k_a/k_d$ model, assuming Langmuir (1:1) binding. The steady-state affinity was determined from curve-fitting to a plot of the Req values, derived from sensorgrams fitted locally, against the concentrations.

Example 4

Figure 7:
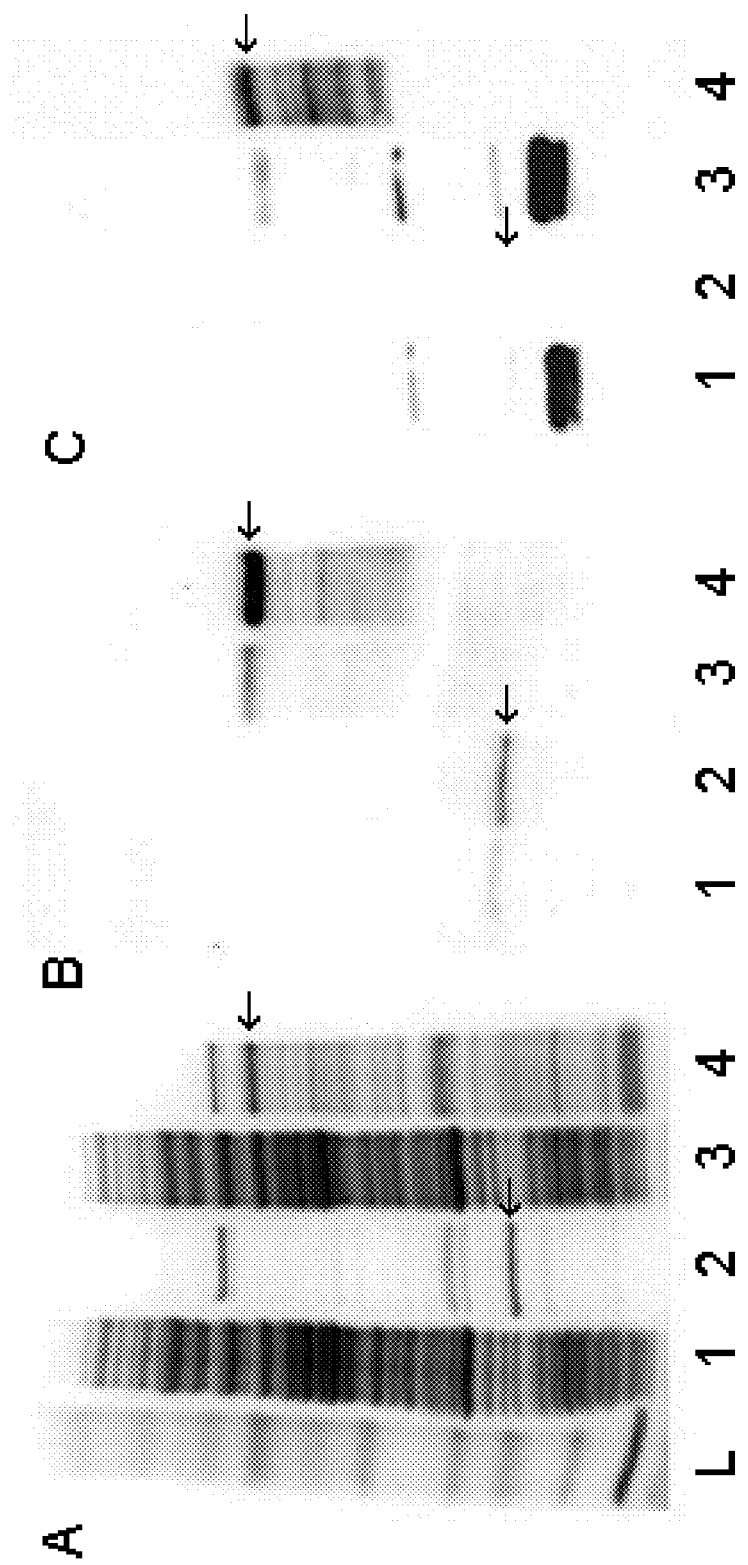
FIG. 7 is a series of three photographs (A-C) of a comparison of the specificity of TTF1 aptamer "A" to a monoclonal anti-Penta-His antibody using protein blot analysis. Lane 1 contains cleared lysate from E. coli expressing the HOX4 homeodomain. Lane 2 contains purified HOX4 homeodomain protein (marked with an arrow). Lane 3 contains cleared lysate from E. coli expressing TTF1. Lane 4 contains purified TTF1 protein (marked with an arrow). (A) 4-20% SDS-PAGE stained with GelCode blue. (B) Blot of material shown in (A) probed with an anti-PentaHis monoclonal antibody. (C) Blot of material shown in (A) probed with the biotinylated TTF1 aptamer "A". Note that the lower dark bands in lanes 1 and 3 of (C) were detected by the secondary probe, Streptavidin-HRP, (not shown).

Comparison of the Specificity of the TTF Aptamer to a Monoclonal Anti-Penta-His Antibody Using Protein Blot Analysis The results of the enzyme-linked assay suggested that the TTF1 AptamerA exhibited specificity for TTF1. In order to verify the specificity and determine whether the aptamer recognized the denatured form of TTF1, as well as to investigate further the potential uses of the aptamer, we performed a protein blot analysis (FIG. 7). The TTF1 AptamerA was indeed able to bind the denatured TTF1 on the blot (FIG. 7C lanes 3, 4) and exhibited very little non-specific binding to the proteins in the cleared *E. coli* lysate or to the purified HOX4 (FIG. 7C lanes 1, 2). The performance of the aptamer was similar to the anti-PentaHis antibody in terms of chemiluminescent signal intensity and specificity (FIG. 7B). Note that the bands in lane 4 of B and C below the major TTF1 band (marked with an arrow) are degradation products of TTF1 as determined by MALDI mass spectromic analysis (not shown). Also, there is an approximately 20 kDa protein in the *E. coli* lysate (FIG. 7C lanes 1, 3) that is recognized by the streptavidin-HRP secondary and not due to cross-reactivity of the aptamer (not shown).

Protein blot analysis with aptamers. Protein samples were prepared for SDS-PAGE by boiling in Laemmli sample buffer and then resolved on denaturing 4-20% polyacrylamide gels using the mini-Protean 3 system (Bio-Rad, Hercules, Calif.). The proteins were either stained with Gelcode Blue (Pierce Biotechnology, Rockford, Ill.) or transferred to PVDF (Schleicher and Schuell, Keene, N.H.). The PVDF membranes were blocked overnight at 4° C. with 5% BSA in PBS-T, and then probed with biotinylated TTF1 AptamerA diluted to 1 µg/mL in 5 mL PBS-T for 2 hours at room temperature with rotation. The blots were washed 3× for 5 min with 10 mL PBS-T and then probed with Streptavidin-HRP diluted 1:10000 in PBS-T. The blots were washed 3× for 5 min before chemiluminescence detection using pico-west substrate (Pierce Biotechnology, Rockford, Ill.). The blots were imaged using a Fluor-S Multi-Imager (Bio-Rad, Hercules, Calif.).

Example 5

TTF1 Aptamer Affinity Purification

Figure 8:
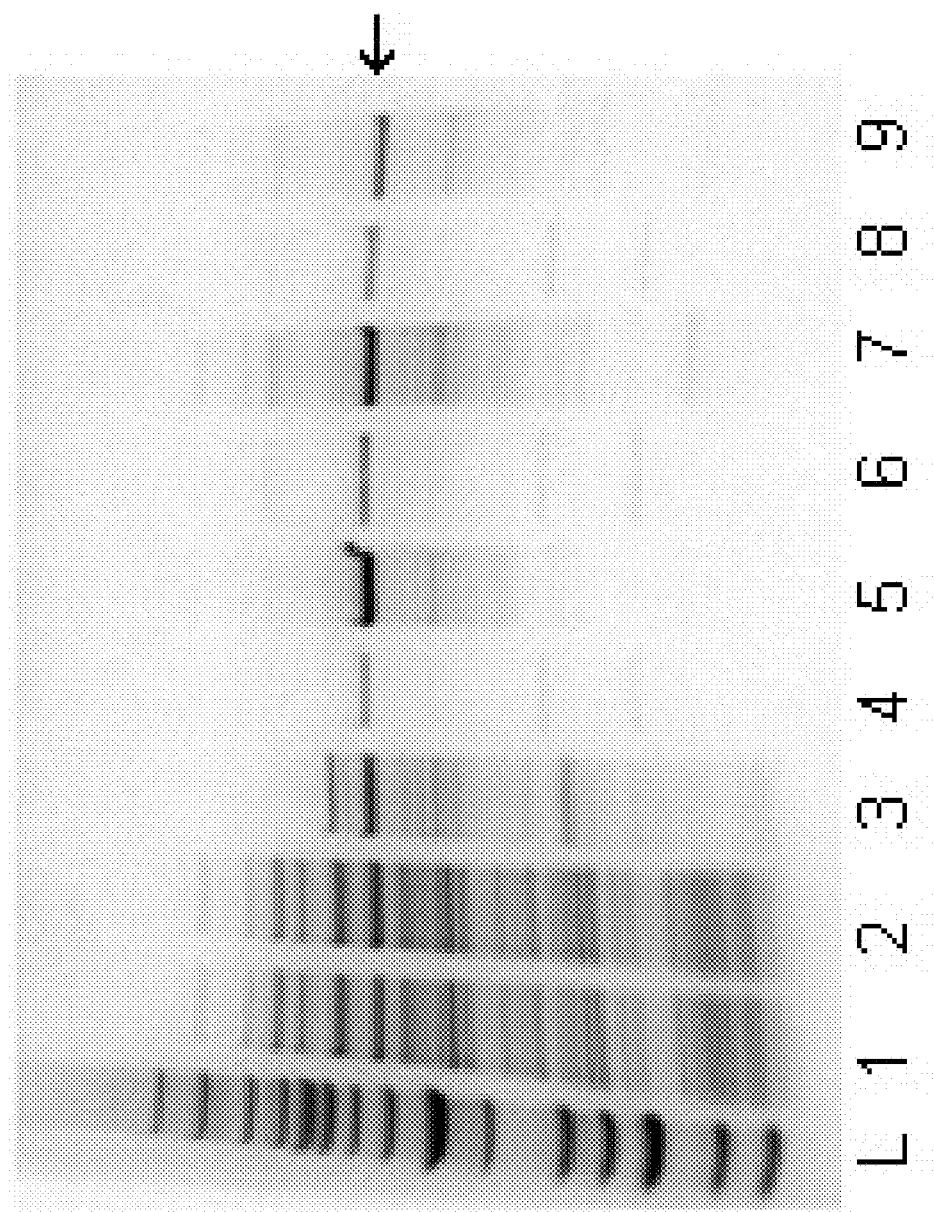
FIG. 8 is a photograph of a nine lane SDS-PAGE analysis of aptamer affinity purification of TTF1 protein from E. coli lysates using biotinylated TTF1 aptamer "A" immobilized on streptavidin magnetic beads. Lane 1 contains cleared lysate from E. coli expressing the protein of interest, and lane 2 contains the cleared lysate spiked with Ni-NTA-purified TTF1 protein (lane 3). Material in lane 4 was from 10 min binding and 2 h elution at 4° C. Material in lane 6 was from 30 min binding and 15 min elution at room temperature. Material in lane 8 was from 5 min binding and 5 min elution at room temperature. After each elution with Benzonase, any remaining protein was removed from the aptamer with 0.1% SDS (Lanes 5, 7 and 9).

Aptamer affinity chromatography was performed from a complex mixture of proteins in the soluble fraction of bacterial lysates using biotinylated aptamers on streptavidin magnetic beads (FIG. 8). Two methods are described, one uses an aptamer that binds a specific protein, TTF1, as an example of purification of untagged proteins from *E. coli* lysates, and another method that uses an aptamer that binds the His6 tag as an example of a general use reagent against any His-tagged protein.

Purification of TTF1 native proteins using specific DNA aptamers. The TTF1 AptamerA was used to purify recombinant TTF1 protein out of the *E. coli* lysate in a single purification step (FIG. 8). Elution of all proteins bound to the TTF1 AptamerA magnetic beads with SDS, which removes all bound proteins from the beads, showed that the purification of TTF1 was highly specific. Referring now to FIG. 8, a nine lane SDS-PAGE analysis was carried out for aptamer affinity purification of TTF1 protein from *E. coli* lysates using biotinylated TTF1 aptamer "A" immobilized on streptavidin magnetic beads. The gel was 4-20% polyacrylamide stained with GELCODE blue. Lane 1 contained cleared lysate from *E. coli* expressing the protein of interest and lane 2 contained the cleared lysate spiked with Ni-NTA purified TTF1 protein (lane 3). Material in lane 4 was from 10 min binding and 2 hr elution at 4° C. Material in lane 6 was from 30 min binding and 15 min elution at room temperature. Material in lane 8 was from 5 min binding and 5 min elution at room temperature. After each elution with Benzonase, any remaining protein was removed from the aptamer with 0.1% SDS (lanes 5, 7, 9).

The generic elution conditions that would be most amenable to high-throughput methods were then tested. Elution of the purified TTF1 from the affinity matrix was inefficient with 1 M NaCl (not shown); therefore we tested elution with a recombinant DNase. The recovery of purified TTF1 with DNase treatment (lanes 4, 6, 8) was approximately 25-50% of the total protein bound to the affinity column as revealed by a subsequent denaturing elution with SDS (lanes 5, 7, 9). The efficiency of elution with DNase was better when the affinity beads were not saturated with TTF1 protein. This is likely due to the accessibility of the aptamer, which may be protected in conditions of saturating amounts of TTF1 protein. Additional optimization for improved elution yield of specific proteins without denaturing could be investigated on a case by case basis. The single-step purification from *E. coli* further illustrates the potential utility of aptamers.

Aptamer affinity purification-TTF1 aptamer. Aptamers immobilized to magnetic beads were utilized for native protein purification. 10 µg of biotinylated TTF1 AptamerA was diluted into 200 µL PBS-T in a PCR tube and heated to 95° C. for 2 min, then immediately placed at 4° C. for 5 min. This material was added to 2 mg M-280 streptavidin magnetic beads (Dynal Biotech, Inc., Brown Deer, Wis.), and 50 µL of 5 M NaCl was added, and the mixed for 30 min with rotation at room temperature. In order to determine the level of non-specific binding to the M-280 beads, we performed the purification with biotin bound, instead of aptamer. The beads were washed 2× with 1 mL PBS-T. 100 µL of cleared lysate from the protein purification described above was spiked with 10 µg of partially purified target protein and then diluted 1:3 with PBS-T. The protein was eluted with DNAse treatment using 12 uL PBS-T containing 50 mM NaCl, 5 mM $MgCl_2$, and 60 units of Benzonase (Novagen, Madison, Wis.). Several binding and elution schemes were tested: 1) 10 min binding at 4° C. and 2 hour nuclease treatment at 4° C.; 2) 30 min binding at 4° C. and 15 min nuclease treatment at room temperature; 3) 5 min binding and 5 min nuclease treatment at room temperature. For each set of conditions, the beads were washed 4× with 1 mL PBS-T containing 600 mM NaCl, and then washed 2× with 1 mL PBS-T containing 50 mM NaCl to adjust the ionic strength for optimal nuclease activity. Protein that remained after nuclease treatment was removed from the aptamer beads with 12 µL of 0.05% SDS. The samples were analyzed by SDS-PAGE on a 4-20% gel that was stained with GelCode blue (Pierce Biotechnology, Rockford, Ill.).

Example 6

Isolation and Selection of His6 Aptamers and their Characterization

The method described below was used to obtain 40 nucleotide DNA oligomers that tightly bind 6 sequential histidine amino acid residues. The target peptide was tagged with biotin to bind the peptide to streptavidin magnetic beads. These peptide bound magnetic beads were then used following the method as described herein and in Example 1. While 5 is likely the minimum number of sequential His residues to be used in the affinity tag, more than 6 His residues may readily be employed. The term "histidine 6" or "His6" or "6His" or "hexahistidine" or "polyhistidine" includes these variations.

Purification of His-tagged proteins using 6His aptamer. The 6H5 aptamer immobilized to magnetic beads was used to purify 5 different recombinant His6-tagged proteins out of *E. coli* lysates with high selectivity in a single purification step. Elution of all 5 proteins bound to the aptamer magnetic beads was achieved under native conditions using imidazole.

Aptamer Affinity Purification-His6 Aptamer.

The proteins ATF, HNF1b, PBX, TTF1, USF1 were expressed in Rosetta (DE3) pLysS cells (Novagen, Madison, Wis.) induced with 1.0 mM IPTG at 37° C. for 4 hours. One liter of culture grown under these conditions was harvested by centrifugation at 5,000×g for 10 min at 4° C. The pellet was resuspended in 30 mL of resuspension buffer (50 mM $Na_2HPO_4$, 300 mM NaCl, 20 mM imidazole, 0.1% Triton X100, 5 mM 2-mercaptoethanol at pH 7.0 with 1 mM PMSF Plus (Roche-Applied-Science, Indianapolis, Ind.), and 1× Protease Inhibitor Cocktail (Sigma Chemicals, St. Louis, Mo.)). The cells were then lysed with the Emulsiflex-C5

(Avestin, Ottawa, Ontario, Canada) homogenizer at 15,000 psi. The lysate was centrifuged at 15,000×g for 25 min at 4° C. to remove insoluble material.

For each protein sample, 10 µg of biotinylated 6H5 aptamer was diluted into 200 µL PBS-T in a PCR tube and heated to 95° C. for 2 min, then immediately placed at 4° C. for 5 min. This material was added to 2 mg M-280 streptavidin magnetic beads (Dynal Biotech, Brown Deer, Wis.), plus 50 µL of 5 M NaCl, and mixed for 30 min at room temperature. The beads were washed 2× with 1 mL PBS-T before use. 1 mL of *E. coli* cleared lysate containing the protein of interest was mixed for 20 min at room temperature with 2 mg M-280 magnetic beads coated with 10 µg of 6H5 aptamer or with 35 µL of Ni-NTA magnetic beads (Qiagen, Valencia, Calif.). The beads were washed 3× with PBS-T containing 500 mM NaCl. Proteins were eluted with 20 uL PBS-T containing 1 M imidazole. Replicate samples were treated with 0.05% SDS to elute all proteins from the beads in order to determine the effectiveness of the imidazole elution. 10 µL of this material was analyzed by SDS-PAGE on a 4-20% gel that was stained with GELCODE blue.

The degenerate sequences of the His6 aptamers isolated are disclosed below:

```
Aptamer 6H5 (approx. 30% of total)
SEQ ID: NO: 14
GGCTTCAGGTTGGTCTGGTTGGGTTTGGCTCCTGTGTACG Aptamer 6H1 (approx. 20% of total)
SEQ ID: NO: 15
GGCAAAAAGGATTGCCCAGGTCTGCTGTCTAGCCGGATTC Aptamer 6H7 (approx. 8% of total)
SEQ ID: NO: 16
GCTATGGGTGGTCTGGTTGGGATTGGCCCCGGGAGCTGGC
```

The sequences, SEQ ID NOS: 14, 15 and 16, were flanked on either ends by the LIC primers (SEQ ID NO: 17 and SEQ ID NO: 18). The percentage of total indicates the percentage of the total final aptamer mixture represented by the particular aptamer, after the complete iterative series of binding, elution and amplification.

FIG. 9 shows a multiple sequence alignment using AlignX (Vector NTI), a modified Clustal W algorithm, of the 3 aptamers that were selected for binding to hexahistidine. The 40 bases of unique sequence, and not the flanking LIC primer sequences, are in the alignment. The bases highlighted in black are found in all three aptamer sequences, and the bases highlighted in grey are found in two of the three aptamer sequences. A consensus pattern generated from the multiple sequence alignment is shown, and is GGCTANNNGGGT-TGGTCTGGTTGGGTTTGGCNCCGGNNTCNG (SEQ ID NO: 21). The aptamer sequences are 31.8% identical and 79.5% conserved.

The selected His6 aptamer sequences were characterized to determine the binding affinity of the aptamer sequence to various target molecules, the kinetics of the good binding affinity and the optimized method of affinity purification. Table 1 summarizes the characterization of selected His6 sequences, 6H1, 6H5 and 6H7. The aptamers were further characterized according to the aptamer binding affinity to known and common proteins using surface plasmon resonance.

The kinetics of the interaction were determined using the method described in Example 3, i.e. surface plasmon resonance (SPR). The biotinylated aptamer to a His6 peptide was immobilized to one flow cell of a streptavidin coated sensor chip. Purified His6 tagged protein was diluted to give a series of concentrations that are injected over the surface. After measuring the on and off rates, the affinity, as described by the equilibrium dissociation constant ($K_D$), is determined globally by fitting to the kinetic simultaneous $k_a/k_d$ model. This is preferably measured by SPR in a device such as a BIAcore or by equilibrium dialysis. The following table describes the characterization of the His6 aptamers.

TABLE 1

Summary of His6 aptamer characterization

| Aptamer | Protein | Binding (SPR) | Kinetics (SPR) | Affinity Purification |
|---------|---------|---------------|----------------|-----------------------|
| 6H5 | PBX | high, unusual | no fit, multimer | ATF, HNF1b, |
|  | USF1 | good, dimer | $K_D$ = 176 nM | PBX, TTF1, |
|  | XF1293 | good | $K_D$ = 30 nM | USF1 |
|  | IDH | poor | | |
| 6H1 | USF1 | good, dimer | $K_D$ = 36 nM | |
|  | XF1293 | very good | $K_D$ = 0.08 nM | |
| 6H7 | XF1293 | good | $K_D$ = 0.4 nM | |
|  | PBX | high, unusual | no fit, multimer | |
|  | XF0749 | good | $K_D$ = 42 nM | |

In the above Table, the first column is the designation of the aptamer, as represented in the above sequences. The next column, "Protein" represents the protein which was his-tagged and tested for binding to the aptamer. The proteins may be further identified as follows:

ATF—NP 005162, activating transcription factor 1 (*Homo sapiens*)

HNF1b—NP 033356, hepatocyte nuclear factor-1 beta (*Homo sapiens*)

PBX—P41778, Pre-B-cell leukemia transcription factor-1 (*ciona intestinalis*)

USF1—P22415, upstream stimulatory factor (*ciona intestinalis*)

TTF1—CAA08756, thyroid transcription factor (*ciona intestinalis*)

XF1293—NP 298582, hypothetical conserved (*Xylella fastidiosa*)

IDH—*E. coli* isocitrate dehydrogenase

XF0749—NP 298039, virulence regulator (*Xylella fastidiosa*)

In the third column, "Binding," the binding of the aptamer to the specific protein, as measured by SPR is characterized. In the case of PBX, for example, the binding was "unusual" in that the data curves could not be fitted because they were 3-4 times the expected response, possibly due to multimerization, aggregation, precipitation or other events that would affect the binding response. The fourth column, "Kinetics," represents the binding of the aptamer to the protein, as measured by SPR. The $K_D$ is a measure of the equilibrium dissociation constant, which describes the "on and off" rates" of the protein-aptamer complex.

Finally, the fifth column, "Affinity purification" shows that aptamer 6H5 was successfully used to affinity purify the listed, tagged proteins by binding to their His6 tag. Each his-tagged protein was purified from an *E. coli* lysate.

Example 7

Use of His6 Aptamers as Capture Agents for SPR or Microarray Format

DNA aptamers are ideal reagents for SPR due to their stability and optimal binding characteristics. We have shown that our 6H5 aptamer works well as a capture agent. FIG. 10 shows schematics for capture methods using the His6 aptamers of Example 6 for SPR experiments. FIG. 10A shows the traditional method using an antibody that binds to the His6 tag. FIG. 10B shows the use of a biotinylated aptamer on a streptavidin chip that binds to the His6 tag. FIG. 10C shows the use of a biotinylated linker primer on a streptavidin chip that binds to the fixed portion of the aptamer by base complementarity.

Figure 11:
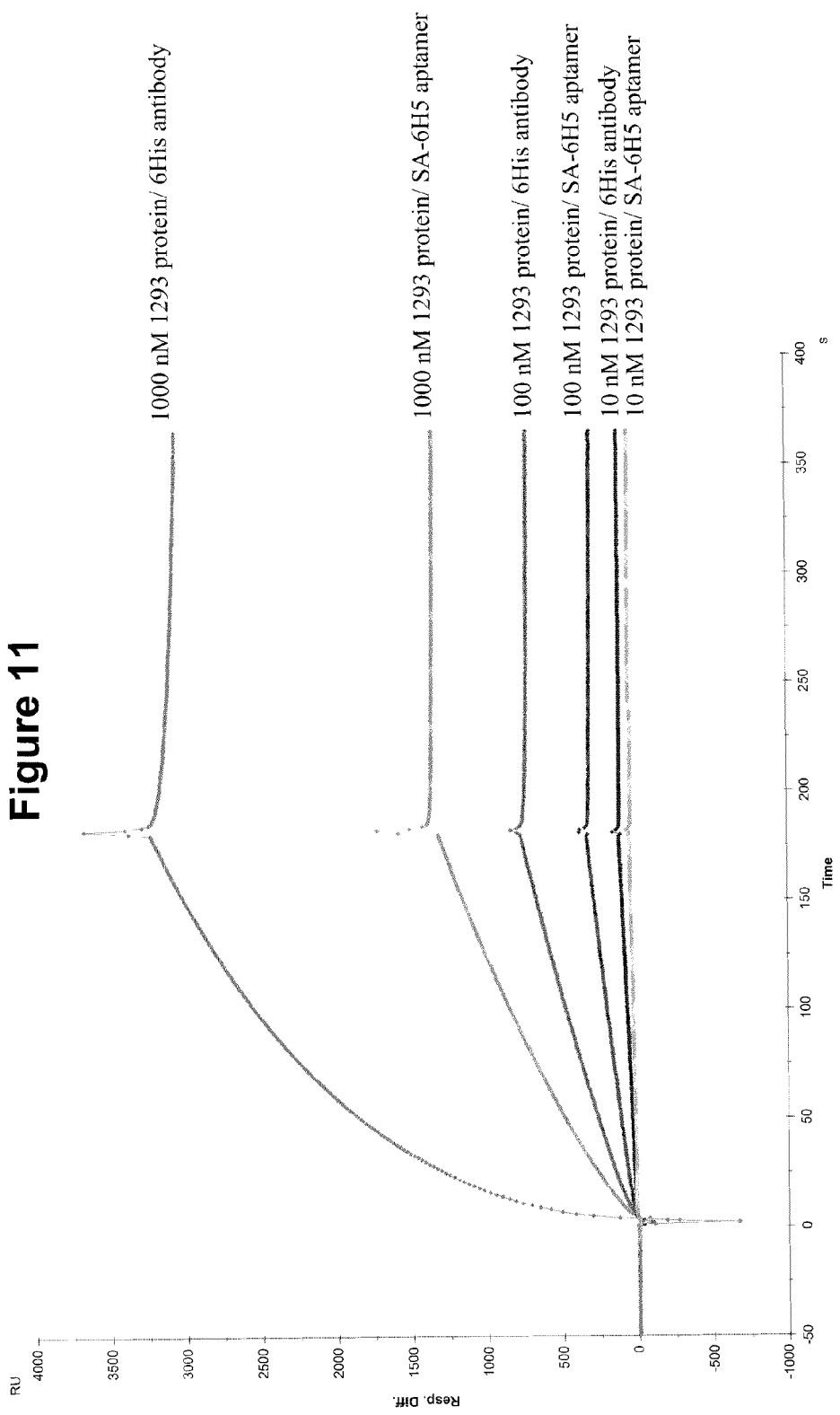
FIG. 11 is a graph showing the association and dissociation of 1293 His-tagged protein from SA-6H5 aptamer vs. 6His antibody.
Figure 12:
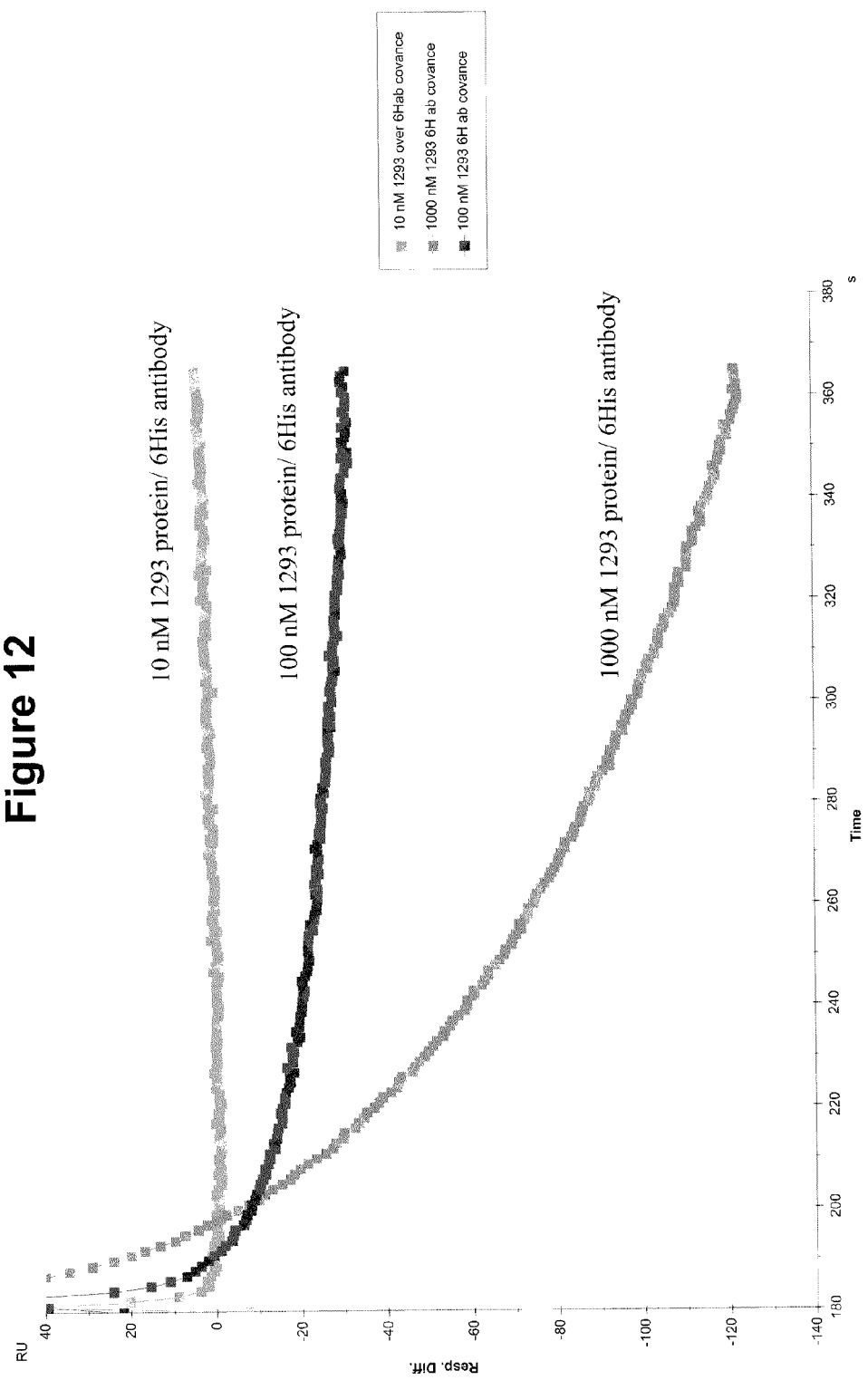
FIG. 12 is a graph showing dissociation curves for 10, 100, and 1000 nM 1293 His-tagged protein from 6His antibody chip.
Figure 13:
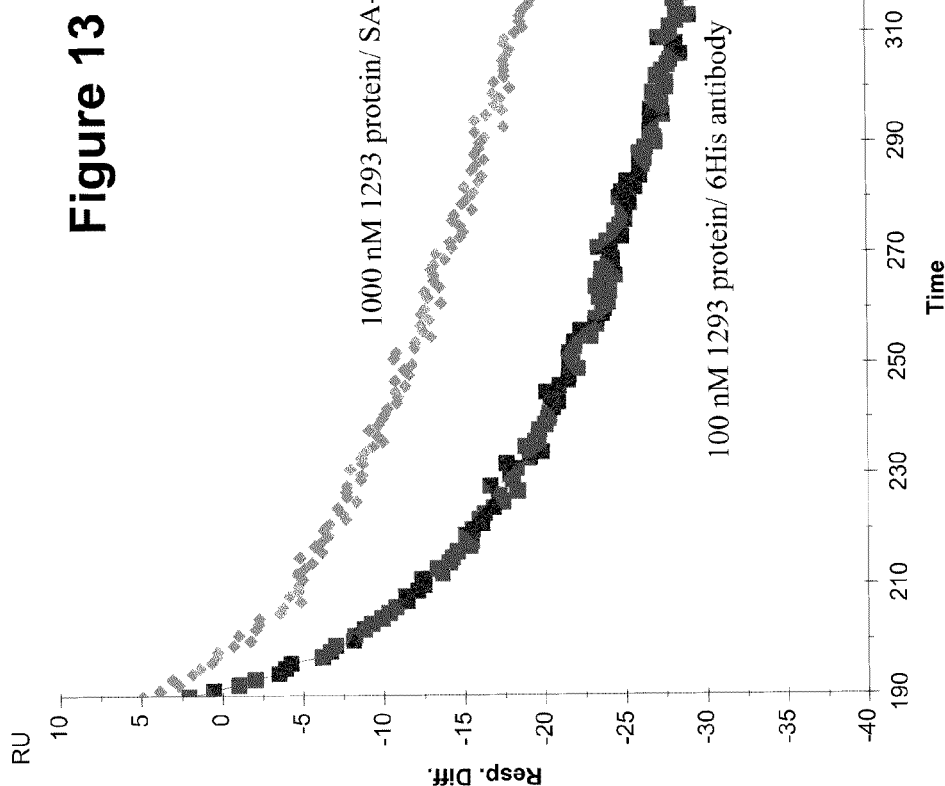
FIG. 13 is a graph showing dissociation curves for 100 nM 1293 His-tagged protein from 6His antibody chip and 1000 nM 1293 His-tagged protein from SA-6H5 aptamer chip. These curves show similar dissociation rates despite the 10-fold higher concentration of protein from the aptamer sample.

Preliminary data (not shown) has shown that most commercially available antibodies (such as PENTAHIS antibody from Qiagen, Valencia, Calif.) display fast off rates that causes baseline drift as the capture protein dissociates from the antibody. It was found that an alternative antibody for the 6His tag (from Covance Research Products, Denver, Pa.) that does not result in significant baseline drift, as described above. The Covance antibody (amine coupled to a BIAcore CM-5 chip) was compared to that of our 6H5 aptamer (SEQ ID NO: 14) (bound to a streptavidin-coated BIAcore chip due to an attached biotin moiety) (FIG. 11). Molar-equivalent amounts of antibody and aptamer bound to the sensor chip (80 fmoles and 72 fmoles, respectively). Samples containing 3 concentrations of His-tagged protein were passed over the chips, and binding and dissociation characteristics were monitored. While the antibody-coated chip bound more protein, comparison of the dissociation rates suggest that the aptamer displays lower baseline drift (FIGS. 12 and 13). This, coupled with the greater stability of the aptamer, demonstrates that the 6H5 aptamer is an ideal capture agent for SPR.

Example 8

Novel Capture Scheme for Aptamer (for SPR or Microarray Chip Surface)

A disadvantage to both strategies, described above, is that the capture agent is irreversibly coupled to the SPR chip (BIAcore, Piscataway, N.J.), making the chip unable to be reused with another capture agent. When using an aptamer or antibody that binds a generic tag, such as the 6His tag, this is less of a disadvantage since the chip can be used with additional proteins that contain the tag. However, if the experiment involves testing a number of antibodies or aptamers, the chip becomes single use. Additionally, there is an added cost associated with generating biotinylated aptamers (as opposed to non-biotinylated ones), therefore it would be advantageous to have a method to couple non-biotinylated aptamers to surfaces such as SPR chips. In a microarray format, this is a major advantage since a large number of aptamers would be bound to the slide surface, which could be made by PCR or oligo synthesis without extra cost.

Herein is described a method to attach non-biotinylated aptamers to coated surfaces, specifically streptavidin-coated surfaces. A biotinylated "linker primer" oligonucleotide was obtained, which contained sequences complementary to portions of the fixed 3' primer sequence of the His6 aptamer sequences. As shown in FIG. 10C, the linker primer binds to a streptavidin-coated sensor chip via the biotin moiety, and captures the aptamer via its complementary sequences.

Figure 14:
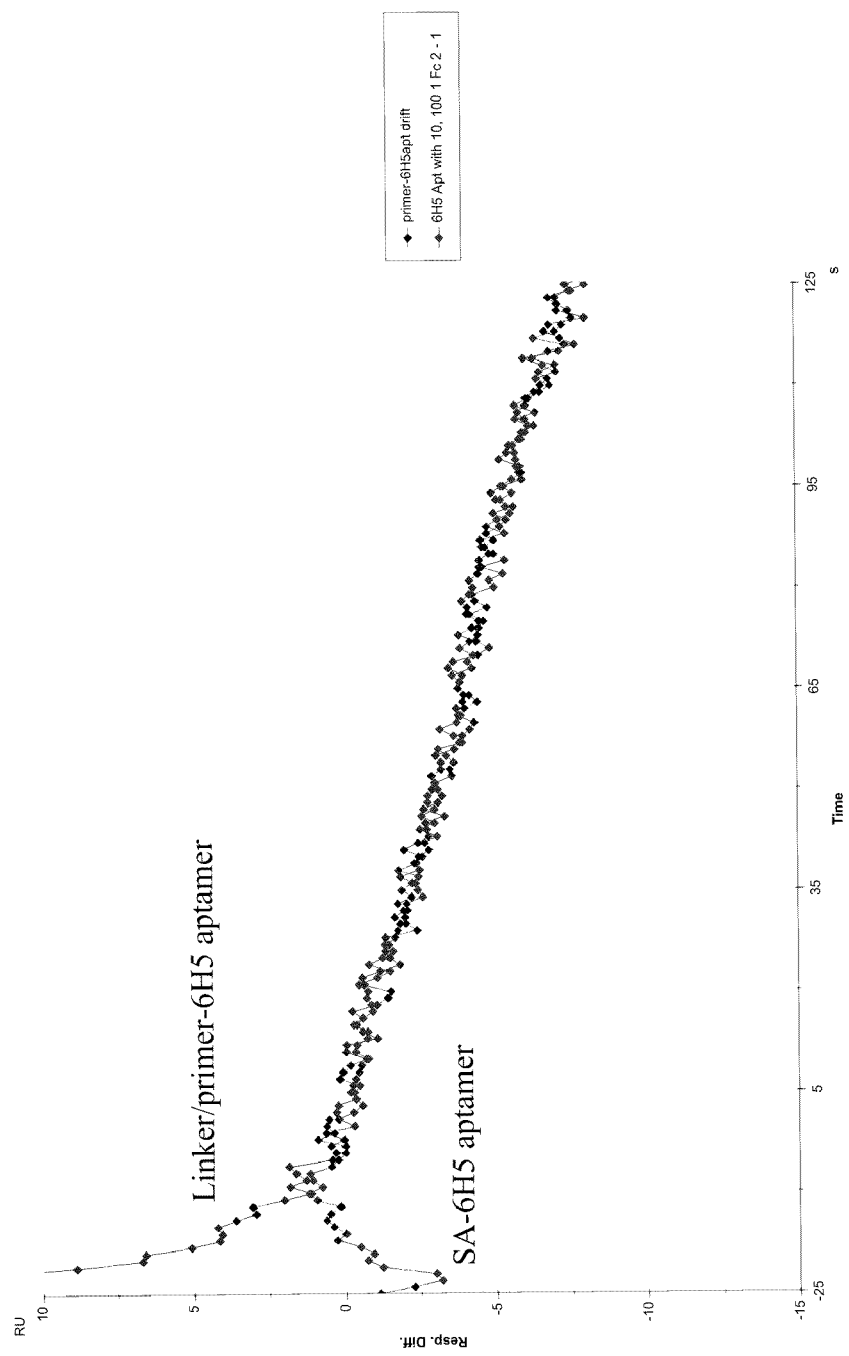
FIG. 14 is a graph showing the baseline drift of 6H5 aptamer immobilized on SA chip via biotin vs. 6H5 aptamer immobilized via complementary linker/primer.

Data shows that the linker primer binds to the BIAcore streptavidin chip at a capacity (saturation) equal to that of the DNA aptamer (52 fmoles, 1.3 ng). When the linker is bound at saturating concentrations, preliminary data suggested that approximately 30% of the linker is accessible for aptamer binding. Dissociation of the aptamer from the linker, however, is extremely slow, displaying characteristics similar to that of the biotinylated aptamer bound directly to the streptavidin chip (2.5 RU/min) (FIG. 14).

Figure 15:
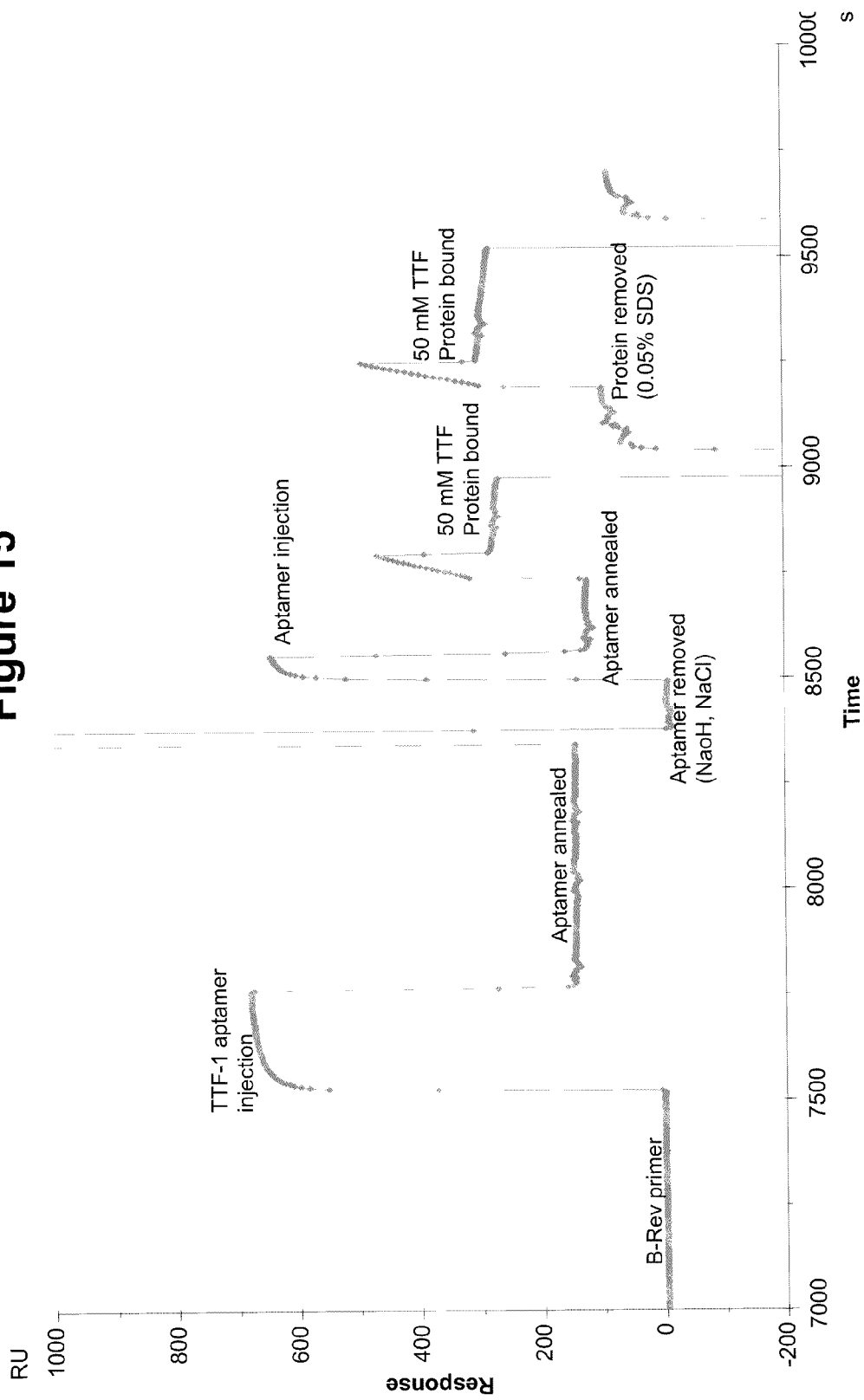
FIG. 15 is a sensorgram of TTF-1 aptamer binding and regeneration from linker/primer and TTF-1 protein binding and regeneration from linker/aptamer complex.

Many SPR applications (such as the determination of binding constants) require that sub-saturating concentrations of capture molecule be used. The linker primer bound at sub-saturating concentrations (0.06 ng) to the sensor chip can bind aptamers at a ratio of approximately 1:1, indicating that the nearly all the linker is accessible as a capture agent (FIG. 15). The aptamer can be removed from the linker with 50 mM NaOH, 1M NaCl, leaving a linker that is able to rebind aptamer efficiently. The bound aptamer is able to capture its protein partner, which can subsequently be removed from the aptamer/linker pair by addition of 0.05% SDS, leaving an aptamer that retains the ability to bind its protein partner.

While the present compositions and processes have been described with reference to specific details of certain exemplary embodiments thereof, it is not intended that such details be regarded as limitations upon the scope of the invention. The present examples, methods, procedures, specific compounds and molecules are meant to exemplify and illustrate the invention and should in no way be seen as limiting the scope of the invention. Any patents or publications mentioned in this specification and below are indicative of levels of those skilled in the art to which the invention pertains and are hereby incorporated by reference to the same extent as if each was specifically and individually incorporated by reference.

What is claimed is:

1. A method for obtaining an aptamer sequence having high affinity to a target molecule, comprising:
   (a) providing a target molecule with a polyhistidine tag, said polyhistidine tag having a binding affinity to magnetic beads;
   (b) binding the target molecule to magnetic beads via a 6His aptamer, wherein the magnetic beads are coated with the 6His aptamer comprising the aptamer sequence of SEQ ID NOS: 14, 15, 16 and/or 21;
   (c) providing a library of degenerate aptamer sequences, wherein each of said degenerate aptamer sequences is flanked by fixed sequences which permit ligation-dependent cloning;
   (d) contacting the magnetic bead-bound target molecule with said library of degenerate aptamer sequences to allow binding of said degenerate aptamer sequences to the target molecule with high affinity, wherein said high affinity has a dissociation constant of at least $10^{-4}$M;
   (e) forming magnetic bead-bound target-aptamer sequence complexes upon binding of said degenerate aptamer sequences to the target molecule with high affinity;
   (f) separating said magnetic bead-bound target-aptamer sequence complexes from the library of non-binding degenerate aptamer sequences;
   (g) separating target-bound degenerate aptamer sequences from said magnetic bead-bound target aptamer sequence complexes to form a pool of high affinity binding aptamer sequences;
   (h) amplifying the high affinity binding aptamer sequences; and
   (i) iteratively repeating steps (b) through (h) a sufficient number of times to result in identification of at least one high affinity binding aptamer sequence having high affinity for the target molecule, thus obtaining an aptamer sequence having high affinity to said target molecule.

2. The method of claim 1 further comprising:
(j) subcloning the high affinity binding aptamer sequence into a plasmid and transforming *E. coli*;
(k) isolating said plasmid containing said high affinity binding aptamer sequence from transformed *E. coli*; and
(l) amplifying and sequencing said cloned high affinity binding aptamer sequence.

3. The method of claim 1 wherein said flanking fixed sequences are primer sequences.

4. The method of claim 2 wherein said amplification is by rolling circle amplification.

5. The method of claim 1, wherein the 6His aptamer consists of SEQ ID NO: 21 and wherein SEQ ID NO: 21 exhibits binding activity to polyhistidine tags.

6. The method of claim 1, wherein the 6His aptamer consists of SEQ ID NO: 14 and wherein SEQ ID NO: 14 exhibits binding activity to polyhistidine tags.

7. The method of claim 1, wherein the 6His aptamer consists of SEQ ID NO: 15 and wherein SEQ ID NO: 15 exhibits binding activity to polyhistidine tags.

8. The method of claim 1, wherein the 6His aptamer consists of SEQ ID NO: 16 and wherein SEQ ID NO: 16 exhibits binding activity to polyhistidine tags.

* * * * *

SEQUENCE LISTING

```
<160> NUMBER OF SEQ ID NOS: 28

<210> SEQ ID NO 1
<211> LENGTH: 88
<212> TYPE: DNA
<213> ORGANISM: Artificial sequence
<220> FEATURE:
<223> OTHER INFORMATION: synthetic basic aptamer sequence
<220> FEATURE:
<221> NAME/KEY: primer_bind
<222> LOCATION: (1)..(18)
<223> OTHER INFORMATION: PCR primer sequence
<220> FEATURE:
<221> NAME/KEY: misc_feature
<222> LOCATION: (19)..(68)
<223> OTHER INFORMATION: n is a, c, g, or t
<220> FEATURE:
<221> NAME/KEY: misc_feature
<222> LOCATION: (19)..(68)
```

```
<223> OTHER INFORMATION: n is a, c, g, or t
<220> FEATURE:
<221> NAME/KEY: misc_feature
<222> LOCATION: (19)..(68)
<223> OTHER INFORMATION: The 50n region represents the degenerate region
      of the aptamer sequence.
<220> FEATURE:
<221> NAME/KEY: primer_bind
<222> LOCATION: (69)..(88)
<223> OTHER INFORMATION: PCR primer sequence

<400> SEQUENCE: 1
ggtattgagg gtcgcatcnn nnnnnnnnnn nnnnnnnnnn nnnnnnnnnn nnnnnnnnnn      60
nnnnnnnnga tggctctaac tctcctct                                        88

<210> SEQ ID NO 2
<211> LENGTH: 18
<212> TYPE: DNA
<213> ORGANISM: Artificial sequence
<220> FEATURE:
<223> OTHER INFORMATION: oligonucleotide sequence

<400> SEQUENCE: 2
ggtattgagg gtcgcatc                                                   18

<210> SEQ ID NO 3
<211> LENGTH: 20
<212> TYPE: DNA
<213> ORGANISM: Artificial sequence
<220> FEATURE:
<223> OTHER INFORMATION: oligonucleotide primer sequence

<400> SEQUENCE: 3
agaggagagt tagagccatc                                                 20

<210> SEQ ID NO 4
<211> LENGTH: 33
<212> TYPE: DNA
<213> ORGANISM: Artificial sequence
<220> FEATURE:
<223> OTHER INFORMATION: Sequence inserted into vector

<400> SEQUENCE: 4
tccggtattg agggtcgctc taactctcct ctg                                  33

<210> SEQ ID NO 5
<211> LENGTH: 18
<212> TYPE: DNA
<213> ORGANISM: Artificial sequence
<220> FEATURE:
<223> OTHER INFORMATION: oligonucleotide sequence

<400> SEQUENCE: 5
ggtattgagg gtcgcatc                                                   18

<210> SEQ ID NO 6
<211> LENGTH: 20
<212> TYPE: DNA
<213> ORGANISM: Artificial sequence
<220> FEATURE:
<223> OTHER INFORMATION: oligonucleotide primer sequence

<400> SEQUENCE: 6
agaggagagt tagagcctta                                                 20

<210> SEQ ID NO 7
<211> LENGTH: 20
```

```
<212> TYPE: DNA
<213> ORGANISM: Artificial sequence
<220> FEATURE:
<223> OTHER INFORMATION: oligonucleotide primer sequence

<400> SEQUENCE: 7
taatacgact cactataggg                                            20

<210> SEQ ID NO 8
<211> LENGTH: 19
<212> TYPE: DNA
<213> ORGANISM: Artificial sequence
<220> FEATURE:
<223> OTHER INFORMATION: oligonucleotide primer sequence

<400> SEQUENCE: 8
gctagttatt gctcagcgg                                             19

<210> SEQ ID NO 9
<211> LENGTH: 40
<212> TYPE: DNA
<213> ORGANISM: Artificial sequence
<220> FEATURE:
<223> OTHER INFORMATION: synthetic degenerate sequence

<400> SEQUENCE: 9
tcaaaagggg tgattgcttg cacaatgaca gggtaggaca                      40

<210> SEQ ID NO 10
<211> LENGTH: 40
<212> TYPE: DNA
<213> ORGANISM: Artificial sequence
<220> FEATURE:
<223> OTHER INFORMATION: synthetic degenerate sequence

<400> SEQUENCE: 10
gatacacggg cggaggaggt ggggggggggt aggtgggtat                     40

<210> SEQ ID NO 11
<211> LENGTH: 40
<212> TYPE: DNA
<213> ORGANISM: Artificial sequence
<220> FEATURE:
<223> OTHER INFORMATION: synthetic degenerate sequence

<400> SEQUENCE: 11
tggctagtgg gtaaggggcg ggagggtgac agggcgatcc                      40

<210> SEQ ID NO 12
<211> LENGTH: 40
<212> TYPE: DNA
<213> ORGANISM: Artificial sequence
<220> FEATURE:
<223> OTHER INFORMATION: synthetic degenerate sequence

<400> SEQUENCE: 12
ttatggggat gaaagtggtg ttcgggttcg ccacttccac                      40

<210> SEQ ID NO 13
<211> LENGTH: 40
<212> TYPE: DNA
<213> ORGANISM: Artificial sequence
<220> FEATURE:
<223> OTHER INFORMATION: synthetic degenerate sequence

<400> SEQUENCE: 13
ttggggtggg agggcgggtt aacaaagata gcgcaacagg                      40
```

<210> SEQ ID NO 14
<211> LENGTH: 40
<212> TYPE: DNA
<213> ORGANISM: Artificial sequence
<220> FEATURE:
<223> OTHER INFORMATION: synthetic degenerate sequence

<400> SEQUENCE: 14
ggcttcaggt tggtctggtt gggtttggct cctgtgtacg                    40

<210> SEQ ID NO 15
<211> LENGTH: 40
<212> TYPE: DNA
<213> ORGANISM: Artificial sequence
<220> FEATURE:
<223> OTHER INFORMATION: synthetic degenerate sequence

<400> SEQUENCE: 15
ggcaaaaagg attgcccagg tctgctgtct agccggattc                    40

<210> SEQ ID NO 16
<211> LENGTH: 40
<212> TYPE: DNA
<213> ORGANISM: Artificial sequence
<220> FEATURE:
<223> OTHER INFORMATION: synthetic degenerate sequence

<400> SEQUENCE: 16
gctatgggtg gtctggttgg gattggcccc gggagctggc                    40

<210> SEQ ID NO 17
<211> LENGTH: 18
<212> TYPE: DNA
<213> ORGANISM: Artificial sequence
<220> FEATURE:
<223> OTHER INFORMATION: oligonucleotide primer sequence

<400> SEQUENCE: 17
ggtattgagg gtcgcatc                                            18

<210> SEQ ID NO 18
<211> LENGTH: 20
<212> TYPE: DNA
<213> ORGANISM: Artificial sequence
<220> FEATURE:
<223> OTHER INFORMATION: oligonucleotide primer sequence

<400> SEQUENCE: 18
gatggctcta actctcctct                                          20

<210> SEQ ID NO 19
<211> LENGTH: 36
<212> TYPE: DNA
<213> ORGANISM: Artificial sequence
<220> FEATURE:
<223> OTHER INFORMATION: oligonucleotide primer sequence

<400> SEQUENCE: 19
ggtattgagg gtcgctcagt tagcccaaag cattcg                        36

<210> SEQ ID NO 20
<211> LENGTH: 43
<212> TYPE: DNA
<213> ORGANISM: Artificial sequence
<220> FEATURE:
<223> OTHER INFORMATION: oligonucleotide primer sequence

```
<400> SEQUENCE: 20
agaggagagt tagagcctta tcggtaaaca ctgtacagga tcg                          43

<210> SEQ ID NO 21
<211> LENGTH: 42
<212> TYPE: DNA
<213> ORGANISM: Artificial sequence
<220> FEATURE:
<223> OTHER INFORMATION: synthetic consensus aptamer degenerate sequence
<220> FEATURE:
<221> NAME/KEY: misc_feature
<222> LOCATION: (6)..(6)
<223> OTHER INFORMATION: N= A, C, or T
<220> FEATURE:
<221> NAME/KEY: misc_feature
<222> LOCATION: (7)..(8)
<223> OTHER INFORMATION: N= A, or nothing
<220> FEATURE:
<221> NAME/KEY: misc_feature
<222> LOCATION: (32)..(32)
<223> OTHER INFORMATION: N= G, T, or C
<220> FEATURE:
<221> NAME/KEY: misc_feature
<222> LOCATION: (37)..(37)
<223> OTHER INFORMATION: N= A, T, or G
<220> FEATURE:
<221> NAME/KEY: misc_feature
<222> LOCATION: (38)..(38)
<223> OTHER INFORMATION: N= T, G, or A
<220> FEATURE:
<221> NAME/KEY: misc_feature
<222> LOCATION: (41)..(41)
<223> OTHER INFORMATION: N= C, T, or nothing

<400> SEQUENCE: 21
ggctannngg gttggtctgg ttgggtttgg cnccggnntc ng                           42

<210> SEQ ID NO 22
<211> LENGTH: 54
<212> TYPE: DNA
<213> ORGANISM: Artificial sequence
<220> FEATURE:
<223> OTHER INFORMATION: synthetic sequence: plasmid pET30a

<400> SEQUENCE: 22
ggagatatac atatgcacca tcatcatcat catgatatcg gatccgaatt cgag              54

<210> SEQ ID NO 23
<211> LENGTH: 55
<212> TYPE: DNA
<213> ORGANISM: Artificial sequence
<220> FEATURE:
<223> OTHER INFORMATION: synthetic sequence: plasmid pET30a

<400> SEQUENCE: 23
cctctatatg tatacgtggt cgtagtagta gtactatagc ctaggcttaa gctcg             55

<210> SEQ ID NO 24
<211> LENGTH: 33
<212> TYPE: DNA
<213> ORGANISM: Artificial sequence
<220> FEATURE:
<223> OTHER INFORMATION: Sequence inserted into vector

<400> SEQUENCE: 24
aggccataac tcccagcgag attgagagga gac                                     33

<210> SEQ ID NO 25
<211> LENGTH: 13
```

```
<212> TYPE: PRT
<213> ORGANISM: Artificial sequence
<220> FEATURE:
<223> OTHER INFORMATION: Factor Xa protease cleavage site

<400> SEQUENCE: 25

Met His His His His His His Ser Gly Ile Glu Gly Arg
1               5                   10

<210> SEQ ID NO 26
<211> LENGTH: 63
<212> TYPE: DNA
<213> ORGANISM: Artificial sequence
<220> FEATURE:
<223> OTHER INFORMATION: final construct of expression vector
<220> FEATURE:
<221> NAME/KEY: gene
<222> LOCATION: (40)..(40)
<223> OTHER INFORMATION: gene inserted at base 40

<400> SEQUENCE: 26
atgcaccatc atcatcatca ttccggtatt gagggtcgct aaggctctaa ctctcctctg      60
gat                                                                    63

<210> SEQ ID NO 27
<211> LENGTH: 63
<212> TYPE: DNA
<213> ORGANISM: Artificial sequence
<220> FEATURE:
<223> OTHER INFORMATION: final construct of expression vector
<220> FEATURE:
<221> NAME/KEY: gene
<222> LOCATION: (40)..(40)
<223> OTHER INFORMATION: gene inserted at base 40

<400> SEQUENCE: 27
tacgtggtag tagtagtagt aaggccataa ctcccagcga ttccgagatt gagaggagac      60
cta                                                                    63

<210> SEQ ID NO 28
<211> LENGTH: 15
<212> TYPE: DNA
<213> ORGANISM: Artificial sequence
<220> FEATURE:
<223> OTHER INFORMATION: Sequence inserted into vector

<400> SEQUENCE: 28
ggtattgagg gtcgc                                                       15
```